(12) United States Patent
Weiss

(10) Patent No.: US 6,277,622 B1
(45) Date of Patent: Aug. 21, 2001

(54) SYNTHETIC POLYNUCLEOTIDES

(75) Inventor: Anthony Steven Weiss, Sydney (AU)

(73) Assignee: The University of Sydney, Sydney (AU)

( * ) Notice: Subject to any disclaimer, the term of this patent is extended or adjusted under 35 U.S.C. 154(b) by 0 days.

(21) Appl. No.: 09/242,095

(22) PCT Filed: Aug. 11, 1997

(86) PCT No.: PCT/AU97/00505

§ 371 Date: Feb. 8, 1999

§ 102(e) Date: Feb. 8, 1999

(87) PCT Pub. No.: WO98/06830

PCT Pub. Date: Feb. 19, 1998

(51) Int. Cl.[7] .............................. C12N 1/20; C12N 9/02; C07H 21/04
(52) U.S. Cl. ...................... 435/252.3; 435/183; 435/189; 435/440; 435/69.1; 435/41; 536/23.1; 536/23.2
(58) Field of Search ................................. 435/183, 189, 435/440, 69.1, 41, 252.3; 536/23.1, 23.2

(56) References Cited

FOREIGN PATENT DOCUMENTS

| 4-021700 | 1/1992 | (JP) . |
| WO94/14958 | 7/1994 | (WO) . |

OTHER PUBLICATIONS

J. Rosenbloom et al, "Elastin Genes and Regulation of Their Expression," in *Critical Reviews in Eukaryotic Gene Expression*, CRC Press Inc., vol. 1, No. 3, pp. 145–156 (1990).

R. Rapaka et al., "Synthesis pf Polypeptide Models of Elastin, Synthesis and Properties of a Cross Linked Polytetrapeptide," *Int. J. Peptide Protein Res.*, 21:352–363 (1983).

S. Yoshifuji et al., "Chemical Conversion of L–α, ω–Diamino Acids to L–ω–Carbamoyl–αamino Acids by Ruthenium Tetroxide Oxidation," *Chem. Pharm. Bull.*, 35(7):2994–3001 (1987).

Z. Indik et al., "Production of Recombinant Human Tropoelastin: Characterization and Demonstration and Chemotactic Activity," *Arch. Biochem. Biophys.*, 280(1):80–86 (Jul. 1990).

V–M. Kahari et al., "Deletion Analyses of 5'–Flanking Region of the Human Elastin Gene, Delineation of Functional Promoter and Regulatory cis–Elements," *J. Biol. Chem.*, 265(16):9485–9490 (Jun. 5, 1990).

Y. Gursky et al., "The Increase in Gene Expression by Introduction of Rare Codons into the C Terminus of the Template," *Gene*, 148:15–21 (1994).

P. Stopien et al., "Synthesis of a Human Insulin Gene, VI. Expression of the Synthetic Proinsulin Gene in Yeast," *Gene*, 24:289–297 (1983).

S. Makrides, "Strategies for Achieving High Level Expression of Genes in *Escherichia coli*," *Microbiological Reviews*, 60(3):512–538 (Sep. 1996).

D.P. Williams et al., "Design, Synthesis and Expression of a Human Interleukin–2 Gene Incorporating the Codon Usage Bias Found in Highly Expressed *Escherichia coli* Genes," *Nucl. Acids. Res.*, 16(22):10453–10467 (1988).

P.M. Sharp and W–H. Li, "The Codon Adaptation Index—A Measure of Directional Synonymous Codon Usage Bias, and Its Potential Applications," *Nucl. Acids. Res.*, 15(3):1281–1294 (Feb. 11, 1987).

P.M. Sharp and W–H. Li, "Codon Usage in Regulatory Genes in *Escherichia coli* does not Reflect Selection for 'Rare' Codons," *Nucl. Acids Res.*, 14(9):7737–7749 (Oct. 10, 1986).

H.G. Khorana, "Total Synthesis of a Gene," *Science*, 203(16):614–625 (Feb. 1979).

M. Mathur and R. Tuli, "Analysis of Codon Usage in Genes for Nitrogen Fixation from Phylogenetically Diverse Diazotrophs," *J. Mol. Evol.*, 32:364–373 (May 1991).

Hamalainen et al. "Molecular cloning of human lysyl oxidase and assignment of the gene to chromosome 5q 23.3–31.2."published Nov. 1991, Genomics, vol. 11 (3); pp. 508–516.

Svinarich et al. "Characterisation of the human lysyl oxidase gene locus."published Jul. 15, 1992, J. Biol. Chem, vol. 267 (20); pp. 14382–14387.

Kenyon, K et al. "A novel human CDNA with a predicted pretein similar to lysyl oxidase maps to chromosome 15q24–q25."published Sep. 5, 1993. J. Biol. Chem, vol. 268 (25), pp. 18435–18437.

Hamalainen et al. "Structure of the human lysyl oxidase gene." published Sep. 1993. Genomics, vol. 17 (3), pp. 544–548.

(List continued on next page.)

*Primary Examiner*—Rebecca E. Prouty
*Assistant Examiner*—Richard Hutson
(74) *Attorney, Agent, or Firm*—Howson and Howson

(57) ABSTRACT

This invention relates to synthetic polynucleotides which encode lysyl oxidase, lysyl oxidase like molecules or variants of these species. The synthetic polynucleotides of the invention permit the expression of functional lysyl oxidase, lysyl oxidase like molecules or variants of these species, typically in good yield. The invention also relates to recombinant DNA molecules containing these, synthetic polynucleotides, to cells containing them and to uses of the expression products.

7 Claims, 12 Drawing Sheets

OTHER PUBLICATIONS

Figure 5:
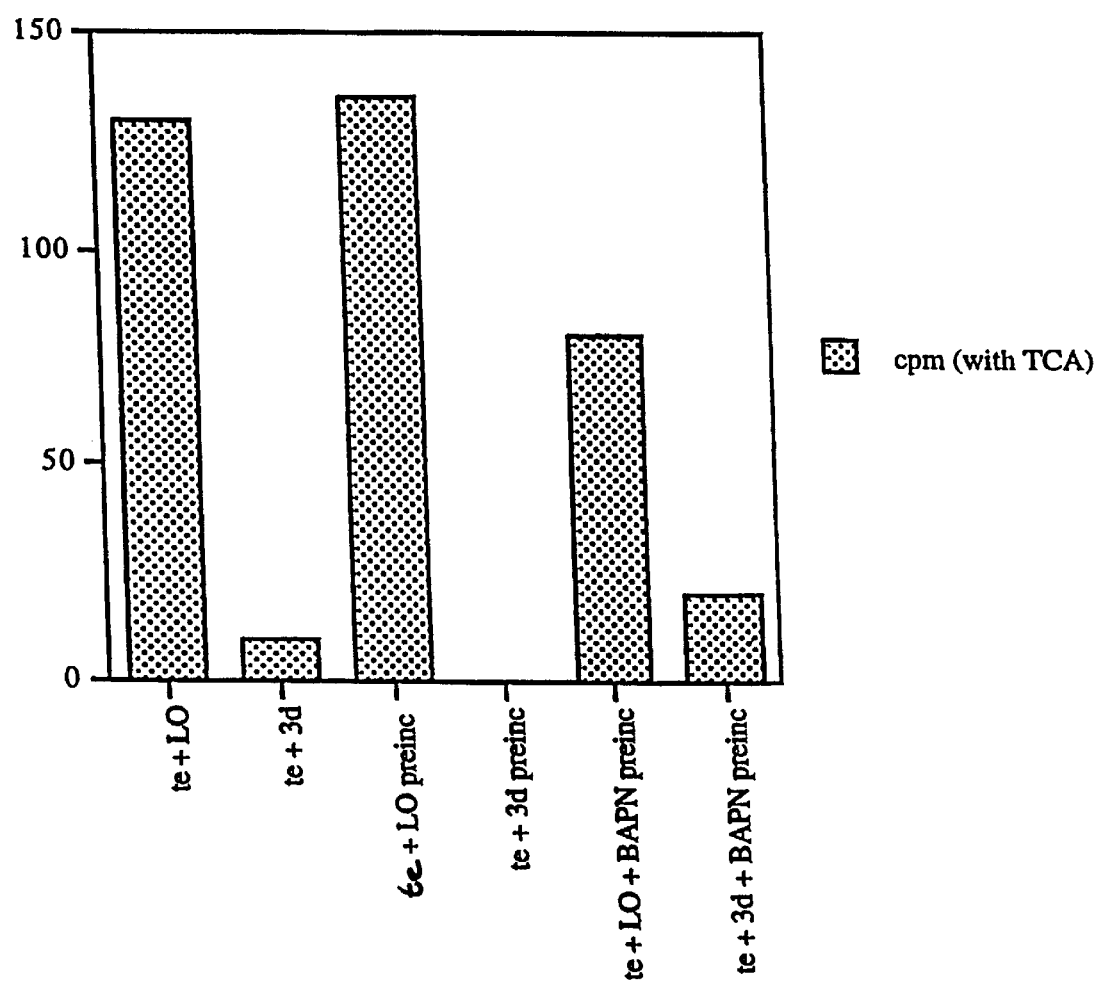

Kim, Y et al. "A new gene with sequence and structure similarity to the gene encoding human lysyl oxidase." published Mar. 31, 1995. J. Biol. Chem, vol. 270(13), pp. 7176–7182.

Ouzzine, M. Et al. "Expression of active, human lysyl oxidase in Escherichia coli." published Dec. 16, 1996. FEBS Lett, vol. 399 (3), pp. 215–219.

Mariani, TJ et al. "The complete derived amino acid sequence of human lysyl oxidase and assignment of the gene to chromosome 5." published 1992. Matrix, vol. 12, pp. 242–248.

Bedell–Hogan, D., Tachman, P., Abrams, W., Rosenbloom, J. and Kagan H. "Oxidation, Cross–linking, and Insolubilization of Recombinant Tropoelastin by Purified Lysyl Oxidase." (May 1993) J. Biol. Chem. 268, 10345–10350.

Boyd, C.D., Marjani, T.J. Kim, Y. and Csiszar, K. The size heterogeneity of human lysyl oxidase mRNA is due to alternate Polyadenylation site and not alternate exon usage. (1995). Mol. Biol. Reports. 21, 95–103.

Bullock W.O., Fernandes J. M. and Short J. M. "XL1–Blue: A High Efficiency Plasmid Transforming recA Escherichia coli Strain With Beta–Galactosidase Selection." (1987) Biotechniques 5, 376–379.

Contente, S., Kenyon, K., Rimoldi, D. and Friedman, R.M. Expression of gene $\pi$g is associated with rversion of NIH 3T3 transformed by LTR–c–H–ras. (1990) Science. 249, 796–798.

Contente, S., Csiszar, K., Kenyon, K. and Friedman, R.M. Structure of the mouse lysyl oxidase gene. (1993) Genomics. 16, 395–400.

Cronshow, A.D., MacBeath, J.R., Shackleton, D.R., Collins, J.F., Fothergill–Gilmore, L.A. and Hulmes, DF. TRAMP (tyrosine rich acidic matrix protein), a protein that co–purifies with lysyl oxidase from porcine skin. Identification of TRAMP as the dermatan sulphate proteoglycan–associated 22K extracellular matrix protein.(1993) Matrix. 13, 255–266.

Cronshaw, A.D., Fothergill–Gilmore, L.A. and Hulmes, D.J. The proteolytic processing site of the precursor of lysyl oxidase. (1995) Biochem. J. 306, 279–284.

Dimaculangan, D.D., Chawla, A., Boak. A., Kagan, H.M. and Lazar, M.A. Retinoic acid prevents down rgulation of ras recision gene/lysyl oxidase early in adipocyte differentiation. (1994) Differentiation. 58, 47–52.

Gacheru, S.N., Trackman, P.C., Shah, M.A., O'Gara, C.Y., Spacciapoli, P., Greenaway, F.T. and Kagan, H.M. Structural and catalytic properties of copper in lysyl oxidase.(Nov. 1990) J. Biol. Chem. 265, 19022–19027.

Gough, J.A. and Murray, N.E. Sequence diversity among related genes for recognition of specific targets in DNA molecules.(1983) J. Mol. Biol. 166,1–19.

Green, R.S., Lieb, M.E., Weintraub, A.S., Gacheru, S.N., Rosenfield, C.L., Shah, S., Kagan, H.M. and Taubman, M.B. Identification of lysyl oxidase and other platelet–derived growth factor–inducible genes in vascular smooth muscle cells by differential screening.(1995) Lab. Invest. 73, 476–482.

Kagan, H.M., Lysyl Oxidase: Mechanism, Regulation and Relation ship to Liver Fibrosis.(1994) Path. Res. Pract. 190, 910–919.

Kagan, H.M. and Cai, P. Isolation of active site peptides of lysyl oxidase.(1995) Meth. Enzymol. 258, 122–132.

Kagan, H.M., Reddy, V.B., Narasimhan, N. and Csiszar, KI. Catalytic properties and structural components of lysyl oxidase. (1995a) Ciba Foundation Symposium. 192, 100–115; discussion 115–121.

Kagan H.M., Reddy, V.B., Panchenko, M.V., Nagan, N., Boak A.M., Gacheru, S.N. and Thomas, K.M. Expression of lysyl oxidase from cDNA constructs in mammalian cells: the propeptide region is not essential to the folding of secretion of functional enzyme.(1995b) J. Cell. Biochem. 59, 329–338.

Kagan, H.M. and Trackman, P.C. Properties and function of lysyl oxidase. (1991) Amer. J. Resp. Cell Mol. Biol. 5, 206–210.

Kane, J.F., et al. Novel in–frame two codon translation hop during synthesis of bovine placental lactogen in a recombinant strain of Esherichia coli. (1992). Nucl. Acids. Res. 20, 6707–6712.

Kenyon, K., Contente, S., Trackman, P.C., Tang, J., Kagan, H.M. and Friedman, R.M. Lysyl oxidase and $\pi$g messenger RNA.(1991) Science. 253, 802.

Kenyon, K., Modi, W.S., Contente, S. and Friedman, R.M. A novel human cDNA with a predicted protein similar to lysyl oxidase maps to chromosome 15q24–q25.(1993) J. Biol. Chem. 268, 18435–18437.

Kim, Y., Boyd, C.D. and Csiszar, K. A new gene with sequence and structural similarity to the gene encoding human lysyl oxidase.(Mar. 1995) J. Biol. Chem. 270, 7176–7182.

Krzyzosiak, W.J., Shindo–Okada, N., Teshima, H., Nakajima K. and Nishimura, S. isolation of genes specifically expressed in flat revertant cells derived from activated ras–transformed NIH 3T3 cells by treatment with azatyrosine. (Jun. 1992) Proc. Natl. Acad. Sci. 89, 4879–4883.

Lipman, D.J. and Pearson, W.R. Rapid and sensitive protein similarity searches.(Mar. 1985) Science 227, 1435–1441.

Martin, S.L., Vrhovski, B. and Weiss, A.S. Total synthesis and expression in escherichia coli of a gene encoding human tropoelastin.(1995) Gene 154, 159–166.

Murray, E.E. Lotzer, J. and Eberle, M. (1989) Codon usage in plant genes. Nucl. Acids Res. 17, 477–498.

Nagan, N. and Kagan, H.M. Modulation of lysyl oxidase activity toward peptidyl lysine by vicinal dicarboxylic amino acid residues. Implications for collagen cross–linking. (Sep. 1994). J. Biol. Chem. 269, 22366–22371.

Newgard, C.B., Nakano, K., Hwang, P.K. and Fletterick, R.J. Sequence analysis of the cDNA encoding human live glycogen phosphorylase reveals tissue–specific codon usage.(Nov. 1986) Proc. Nat. Acad. Sci. 83, 8132–8136.

Palcic, M.M., Scaman, C.H. and Alton, G. Stereochemistry and cofactor identity status of semicarbazide–sensitive amine oxidases.(1995) Prog. Brain Res. 106, 41–47.

Paz, M.A., Fluckiger, R., Boak, A. Kagan, h.M. and Gallop, P.M. Specific detection of quinoproteins by redox–cycling staining.(Jan. 1991) J. Biol. Chem. 266, 689–692.

Shackleton, D.R. and Hulmes, D.J. Purification of lysyl oxidase from piglet skin by selective interaction with Sephacryl S–200.(1990) Biochem. J. 266, 917–919.

Shah, M.A., Trackman, P.C., Gallop, P.M. and Kagan, H.M. (Jun. 1993) Reaction of lysyl oxidase with trans–2–phenycyclopropylamine. J. Biol. Chem. 268,11580–11585.

Shibanuma, M., Mashimo, J., Mita A., Kuroki, T. and Nose, K. cloning from a mouse osteoblastic cell line of a set of transforming–growth–factor–beta 1–regulated genes, one of which seems to encode a follistatin–related polypeptide.(1993) *Eur. J. Biochem.* 217, 13–19.

Studier, F.W., Rosenberg, A.H., Dunn, J.J. and Dubendorff, J.W. use of T7 RNA polymerase to direct expression of cloned genes.(1990) *Meth. Enzymol.* 185m 60–89.

Tanizawa, K. Biogenesis of novel quinone coenzymes.(1995) *J. Biochem.* 118, 671–678.

Trackman, P.C., Pratt, A.M., Wolanski, A., Tang, S.S., Offner, G.D., Troxler, R.F and Kagan,H.M. Cloning of rat aorta lysyl oxidase cDNA: complete codons and predicted amino acid sequence.(1990) *Biochemistry* 29, 4863–4870 [published erratum appears in (1991) *Biochemistry* 30, 8282].

Williamson, P.R., Moog, R.S., Dooley, D.M. and Kagan, H.M. Evidence for pyrroloquinolinequinone as the carbonyl cofactor in lysyl oxidase by absorption and resonance Raman spectroscopy.(Dec. 1986) *J. Biol.Chem.* 261, 16302–16305.

Wu, Y., Rich, C.B., Lincecum, J., Trackman, P.C., Kagan, H.M. and Foster, J.A. Characterization and developmental expression of chick aortic lysyl oxidase. (Dec. 1992) *J. Biol. Chem.* 267, 24199–24206.

Zhang, S.P., Zubay, G. and Goldman, E. (1991) Low–usage codons in Escherichia coli, yeast, fruit fly and primates. *Gene.* 105, 61–72.

Wang, S.X., Mure, M., Medzihradsky, K.F., Burlingame, A.L., Brown, D.E. Dooley, D.M., Smith, A. J., Kagan, H.M. and Klinman, J.P. A cross linked cofactor in lysyl oxidase: redox function for amino acid side chains.(Aug. 1996) *Science.* 273, 1078–1084.

Trackman, P.C. and Kagan, H.M. Nonpeptidyl amine inhibitors are substrates of lysyl oxidase.(Aug. 1979) *J. Biol. Chem.* 254, 7831–7836.

Reiser, K., et al. Enzymatic and nonenzymatic cross–linking of collagen and elastin. (Apr. 1992). *FASEB Journal*, 6, 2439–2449.

Eyre, D.R., et al. Cross–Linking in Collagen and Elastin. (1984). *Ann. Rev. Biochem.* 53, 717–48.

```
1/1                                              31/11
ATG CGC TTC GCC TGG ACC GTG CTC CTG CTC GGG CCT TTG CAG CTC TGC GCG CTA GTG CAC
 M   R   F   A   W   T   V   L   L   L   G   P   L   Q   L   C   A   L   V   H
61/21                                            91/31
TGC GCC CCT CCC GCC GCC GGC CAA CAG CAG CCC CCG CGC GAG CCG CCG GCG GCT CCG GGC
 C   A   P   P   A   A   G   Q   Q   Q   P   P   R   E   P   P   A   A   P   G
121/41                                           151/51
GCC TGG CGC CAG CAG ATC CAA TGG GAG AAC AAC GGG CAG GTG TTC AGC TTG CTG AGC CTG
 A   W   R   Q   Q   I   Q   W   E   N   N   G   Q   V   F   S   L   L   S   L
181/61                                           211/71
GGC TCA CAG TAC CAG CCT CAG CGC CGC CGG GAC CCG GGC GCC GCC GTC CCT GGT GCA GCC
 G   S   Q   Y   Q   P   Q   R   R   R   D   P   G   A   A   V   P   G   A   A
241/81                                           271/91
AAC GCC TCC GCC CAG CAG CCC CGC ACT CCG ATC CTG CTG ATC CGC GAC AAC CGC ACC GCC
 N   A   S   A   Q   Q   P   R   T   P   I   L   L   I   R   D   N   R   T   A
301/101                                          331/111
GCG GCG CGA ACG CGG ACG GCC GGC TCA TCT GGA GTC ACC GCT GGC CGC CCC AGG CCC ACC
 A   A   R   T   R   T   A   G   S   S   G   V   T   A   G   R   P   R   P   T
361/121                                          391/131
GCC CGT CAC TGG TTC CAA GCT GGC TAC TCG ACA TCT AGA GCC CGC GAA CGT GGC GCC TCG
 A   R   H   W   F   Q   A   G   Y   S   T   S   R   A   R   E   R   G   A   S
421/141                                          451/151
CGC GCG GAG AAC CAG ACA GCG CCG GGA GAA GTT CCT GCG CTC AGT AAC CTG CGG CCG CCC
 R   A   E   N   Q   T   A   P   G   E   V   P   A   L   S   N   L   R   P   P
481/161                                          511/171
AGC CGC GTG GAC GGC ATG GTG GGC GAC GAC CCT TAC AAC CCC TAC AAG TAC TCT GAC GAC
 S   R   V   D   G   M   V   G   D   D   P   Y   N   P   Y   K   Y   S   D   D
541/181                                          571/191
AAC CCT TAT TAC AAC TAC TAC GAT ACT TAT GAA AGG CCC AGA CCT GGG GGC AGG TAC CGG
 N   P   Y   Y   N   Y   Y   D   T   Y   E   R   P   R   P   G   G   R   Y   R
601/201                                          631/211
CCC GGA TAC GGC ACT GGC TAC TTC CAG TAC GGT CTC CCA GAC CTG GTG GCC GAC CCC TAC
 P   G   Y   G   T   G   Y   F   Q   Y   G   L   P   D   L   V   A   D   P   Y
661/221                                          691/231
TAC ATC CAG GCG TCC ACG TAC GTG CAG AAG ATG TCC ATG TAC AAC CTG AGA TGC GCG GCG
 Y   I   Q   A   S   T   Y   V   Q   K   M   S   M   Y   N   L   R   C   A   A
721/241                                          751/251
GAG GAA AAC TGT CTG GCC AGT ACA GCA TAC AGG GCA GAT GTC AGA GAT TAT GAT CAC AGG
 E   E   N   C   L   A   S   T   A   Y   R   A   D   V   R   D   Y   D   H   R
781/261                                          811/271
GTG CTG CTC AGA TTT CCC CAA AGA GTG AAA AAC CAA GGG ACA TCA GAT TTC TTA CCC AGC
 V   L   L   R   F   P   Q   R   V   K   N   Q   G   T   S   D   F   L   P   S
841/281                                          871/291
CGA CCA AGA TAT TCC TGG GAA TGG CAC AGT TGT CAT CAA CAT TAC CAC AGT ATG GAT GAG
 R   P   R   Y   S   W   E   W   H   S   C   H   Q   H   Y   H   S   M   D   E
901/301                                          931/311
TTT AGC CAC TAT GAC CTG CTT GAT GCC AAC ACC CAG AGG AGA GTG GCT GAA GGC CAC AAA
 F   S   H   Y   D   L   L   D   A   N   T   Q   R   R   V   A   E   G   H   K
```

Fig. 1(1)

```
961/321                                          991/331
GCA AGT TTC TGT CTT GAA GAC ACA TCC TGT GAC TAT GGC TAC CAC AGG CGA TTT GCA TGT
 A   S   F   C   L   E   D   T   S   C   D   Y   G   Y   H   R   R   F   A   C
1021/341                                         1051/351
ACT GCA CAC ACA CAG GGA TTG AGT CCT GGC TGT TAT GAT ACC TAT GGT GCA GAC ATA GAC
 T   A   H   T   Q   G   L   S   P   G   C   Y   D   T   Y   G   A   D   I   D
1081/361                                         1111/371
TGC CAG TGG ATT GAT ATT ACA GAT GTA AAA CCT GGA AAC TAT ATC CTA AAG GTC AGT GTA
 C   Q   W   I   D   I   T   D   V   K   P   G   N   Y   I   L   K   V   S   V
1141/381                                         1171/391
AAC CCC AGC TAC CTG GTT CCT GAA TCT GAC TAT ACC AAC AAT GTT GTG CGC TGT GAC ATT
 N   P   S   Y   L   V   P   E   S   D   Y   T   N   N   V   V   R   C   D   I
1201/401                  1231/411
CGC TAC ACA GGA CAT CAT GCG TAT GCC TCA GGC TGC ACA ATT TCA CCG TAT
 R   Y   T   G   H   H   A   Y   A   S   G   C   T   I   S   P   Y
```

Fig. 1(2)

BamHI

```
2/                                      31/11
GA TCC CAG CAG CAG CCG CCG CGT GAA CCG CCG GCT GCT CCG GGT GCT TGG CGT CAG CAG
   S   Q   Q   Q   P   P   R   E   P   P   A   A   P   G   A   W   R   Q   Q
61/21                                   91/31
ATC CAG TGG GAA AAC AAC GGT CAG GTT TTC TCC CTG CTG TCC CTG GGT TCC CAG TAC CAG
 I   Q   W   E   N   N   G   Q   V   F   S   L   L   S   L   G   S   Q   Y   Q
121/41                                  151/51
CCG CAG CGT CGT CGT GAC CCG GGT GCT GCT GTT CCG GGT GCT GCT AAC GCT TCC GCT CAG
 P   Q   R   R   R   D   P   G   A   A   V   P   G   A   A   N   A   S   A   Q
181/61                                  211/71
CAG CCG CGT ACC CCG ATC CTG CTG ATC CGT GAC AAC CGT ACC GCG GCC GCT CGT ACC CGT
 Q   P   R   T   P   I   L   L   I   R   D   N   R   T   A   A   A   R   T   R
```

PstI

```
241/81                                  271/91
ACC GCT GGT TCC TCC GGT GTT ACT GCA GGT CGT CCG CGT CCG ACC GCG CGC CAC TGG TTC
 T   A   G   S   S   G   V   T   A   G   R   P   R   P   T   A   R   H   W   F
301/101                                 331/111
CAG GCT GGT TAC TCC ACC TCC CGT GCT CGT GAA GCT GGT GCT TCC CGT GCT GAA AAC CAG
 Q   A   G   Y   S   T   S   R   A   R   E   A   G   A   S   R   A   E   N   Q
361/121                                 391/131
ACC GCT CCG GGT GAA GTT CCA GCG CTG TCC AAC CTG CGT CCG CCG TCC CGT GTT GAC GGT
 T   A   P   G   E   V   P   A   L   S   N   L   R   P   P   S   R   V   D   G
421/141                                 451/151
ATG GTT GGT GAC GAC CCG TAC AAC CCG TAC AAG TAC TCC GAC GAC AAC CCG TAC TAC AAC
 M   V   G   D   D   P   Y   N   P   Y   K   Y   S   D   D   N   P   Y   Y   N
```

KpnI

```
481/161                                 511/171
TAC TAC GAC ACC TAC GAG CGC CCG CGT CCG GGT GGT CGT TAC CGT CCG GGT TAC GGT ACC
 Y   Y   D   T   Y   E   R   P   R   P   G   G   R   Y   R   P   G   Y   G   T
541/181                                 571/191
GGT TAC TTC CAG TAC GGT CTG CCG GAC CTG GTT GCT GAC CCG TAC TAC ATC CAG GCT TCC
 G   Y   F   Q   Y   G   L   P   D   L   V   A   D   P   Y   Y   I   Q   A   S
```

Fig. 2(1)

```
601/201                                    631/211
ACC TAC GTT CAG AAA ATG TCC ATG TAC AAC CTG CGT TGC GCT GCT GAA GAA AAC TGC CTG
 T   Y   V   Q   K   M   S   M   Y   N   L   R   C   A   A   E   E   N   C   L
661/221                                    691/231
GCT TCC ACC GCT TAC CGT GCT GAC GTT CGT GAC TAC GAC CAC CGT GTT CTG CTG CGT TTC
 A   S   T   A   Y   R   A   D   V   R   D   Y   D   H   R   V   L   L   R   F
721/241                                    751/251
CCG CAG CGT GTT AAA AAC CAG GGC ACC TCC GAC TTC CTG CCG TCC CGT CCG CGT TAC TCC
 P   Q   R   V   K   N   Q   G   T   S   D   F   L   P   S   R   P   R   Y   S
```

EcoRI
```
781/261                                    811/271
TGG GAA TGG CAC TCC TGC CAC CAG CAC TAC CAC TCC ATG GAC GAA TTC TCC CAC TAC GAC
 W   E   W   H   S   C   H   Q   H   Y   H   S   M   D   E   F   S   H   Y   D
841/281                                    871/291
CTG CTG GAC GCT AAC ACC CAG CGT CGT GTT GCT GAA GGT CAC AAA GCT TCC TTC TGC CTG
 L   L   D   A   N   T   Q   R   R   V   A   E   G   H   K   A   S   F   C   L
901/301                                    931/311
GAA GAC ACC TCC TGC GAC TAC GGT TAC CAC CGT CGT TTC GCT TGC ACC GCT CAC ACC CAG
 E   D   T   S   C   D   Y   G   Y   H   R   R   F   A   C   T   A   H   T   Q
961/321                                    991/331
GGT CTG TCC CCG GGT TGC TAC GAC ACC TAC GGT GCT GAC ATC GAC TGC CAG TGG ATC GAC
 G   L   S   P   G   C   Y   D   T   Y   G   A   D   I   D   C   Q   W   I   D
1021/341                                   1051/351
ATC ACC GAC GTT AAA CCG GGT AAC TAC ATC CTG AAA GTT TCC GTT AAC CCG TCC TAC CTG
 I   T   D   V   K   P   G   N   Y   I   L   K   V   S   V   N   P   S   Y   L
1081/361                                   1111/371
GTT CCG GAA TCC GAC TAC ACC AAC AAC GTG GTT CGT TGC GAT ATC CGT TAC ACC GGT CAC
 V   P   E   S   D   Y   T   N   N   V   V   R   C   D   I   R   Y   T   G   H
```

BamHI
```
1141/381                   1171/391
CAC GCT TAC GCT TCC GGT TGC ACC ATC TCC CCG TAC TAA TGA TAG
 H   A   Y   A   S   G   C   T   I   S   P   Y   *   *   *
```

Fig. 2(2)

```
 81 CCAACAGCAGCCCCCGCGCGAGCCGCCGGCGGCTCCGGGCGCCTGGCGCC 130
    ||| ||||||||| ||||| || ||||||||| |||||||| || |||||| |
  6 CCAGCAGCAGCCGCCGCGTGAACCGCCGGCTGCTCCGGGTGCTTGGCGTC  55

131 AGCAGATCCAATGGGAGAACAACGGGCAGGTGTTCAGCTTGCTGAGCCTG 180
    |||||||||| ||||| ||||||||| ||||| ||| | ||||| ||||
 56 AGCAGATCCAGTGGGAAAACAACGGTCAGGTTTTCTCCCTGCTGTCCCTG 105

181 GGCTCACAGTACCAGCCTCAGCGCCGCCGGGACCCGGGCGCCGCCGTCCC 230
    || || |||||||||| ||||| || || |||||||| || || || ||
106 GGTTCCCAGTACCAGCCGCAGCGTCGTCGTGACCCGGGTGCTGCTGTTCC 155

231 TGGTGCAGCCAACGCCTCCGCCCAGCAGCCCCGCACTCCGATCCTGCTGA 280
    ||||| || |||||| ||||| |||||||| || || ||||||||||||
156 GGGTGCTGCTAACGCTTCCGCTCAGCAGCCGCGTACCCCGATCCTGCTGA 205

281 TCCGCGACAACCGCACCGCCGCGGCGCGAACGCGGACGGCCGGCTCATCT 330
    |||| |||||||| ||||| || || || || || || || || || ||
206 TCCGTGACAACCGTACCGCGGCCGCTCGTACCCGTACCGCTGGTTCCTCC 255

331 GGAGTCACCGCTGGCCGCCCCAGGCCCACCGCCCGTCACTGGTTCCAAGC 380
    || || |||||||| || ||  | || ||||| || |||||||||| ||
256 GGTGTTACCGCTGGTCGTCCGCGTCCGACCGCGCGCCACTGGTTCCAGGC 305

381 TGGCTACTCGACATCTAGAGCCCGCGAACGTGGCGCCTCGCGCGCGGAGA 430
    ||| |||||| || ||  | || || |||  ||| || || || || || |
306 TGGTTACTCCACCTCCCGTGCTCGTGAAGCTGGTGCTTCCCGTGCTGAAA 355

431 ACCAGACAGCGCCGGGAGAAGTTCCTGCGCTCAGTAACCTGCGGCCGCCC 480
    ||||||| || |||||| |||||||| ||||||     |||||||| ||||| |||||
356 ACCAGACCGCTCCGGGTGAAGTTCCAGCGCTGTCCAACCTGCGTCCGCCG 405

481 AGCCGCGTGGACGGCATGGTGGGCGACGACCCTTACAACCCCTACAAGTA 530
    ||| || |||||| ||||| || |||||||| |||||||| ||||||||
406 TCCCGTGTTGACGGTATGGTTGGTGACGACCCGTACAACCCGTACAAGTA 455

531 CTCTGACGACAACCCTTATTACAACTACTACGATACTTATGAAAGGCCCA 580
    ||| |||||||||| || |||||||||||||||| || || || | ||
456 CTCCGACGACAACCCGTACTACAACTACTACGACACCTACGAGCGCCCGC 505

581 GACCTGGGGGCAGGTACCGGCCCGGATACGGCACTGGCTACTTCCAGTAC 630
    | || || || | |||| || || ||||| || || ||||||||||||
506 GTCCGGGTGGTCGTTACCGTCCGGGTTACGGTACCGGTTACTTCCAGTAC 555

631 GGTCTCCCAGACCTGGTGGCCGACCCCTACTACATCCAGGCGTCCACGTA 680
    ||||| || |||||||| || ||||||||||||||||||| ||||| ||
556 GGTCTGCCGGACCTGGTTGCTGACCCGTACTACATCCAGGCTTCCACCTA 605
```

Fig.3(1)

```
 681 CGTGCAGAAGATGTCCATGTACAACCTGAGATGCGCGGCGGAGGAAAACT  730
     ||| |||||| |||||||||||||||||| | ||||| || || |||||||
 606 CGTTCAGAAAATGTCCATGTACAACCTGCGTTGCGCTGCTGAAGAAAACT  655

731 GTCTGGCCAGTACAGCATACAGGGCAGATGTCAGAGATTATGATCACAGG  780
     | |||||    || || ||| | || || ||  | || || || ||| |
 656 GCCTGGCTTCCACCGCTTACCGTGCTGACGTTCGTGACTACGACCACCGT  705

781 GTGCTGCTCAGATTTCCCCAAAGAGTGAAAAACCAAGGGACATCAGATTT  830
     || |||||  | || ||  | || ||||||||| || || || || ||
 706 GTTCTGCTGCGTTTCCCGCAGCGTGTTAAAAACCAGGGTACCTCCGACTT  755

831 CTTACCCAGCCGACCAAGATATTCCTGGGAATGGCACAGTTGTCATCAAC  880
     | | ||  ||| || | || |||||||||||||||||  || || || |
 756 CCTGCCGTCCCGTCCGCGTTACTCCTGGGAATGGCACTCCTGCCACCAGC  805

881 ATTACCACAGTATGGATGAGTTTAGCCACTATGACCTGCTTGATGCCAAC  930
     | ||||||  ||||| || ||  ||||||  |||||| |||||| | |||
 806 ACTACCACTCCATGGACGAATTCTCCCACTACGACCTGCTGGACGCTAAC  855

931 ACCCAGAGGAGAGTGGCTGAAGGCCACAAAGCAAGTTTCTGTCTTGAAGA  980
     ||||||  |  | || |||||||| |||||||  ||||| ||  |||||
 856 ACCCAGCGTCGTGTTGCTGAAGGTCACAAAGCTTCCTTCTGCCTGGAAGA  905

981 CACATCCTGTGACTATGGCTACCACAGGCGATTTGCATGTACTGCACACA 1030
     ||| ||||| |||| || || || || |  || || || || || ||||
 906 CACCTCCTGCGACTACGGTTACCACCGTCGTTTCGCTTGCACCGCTCACA  955

1031 CACAGGGATTGAGTCCTGGCTGTTATGATACCTATGGTGCAGACATAGAC 1080
     | |||||  ||  || || || || || |||  |||| || ||| | ||
 956 CCCAGGGTCTGTCCCCGGGTTGCTACGACACCTACGGTGCTGACATCGAC 1005

1081 TGCCAGTGGATTGATATTACAGATGTAAAACCTGGAAACTATATCCTAAA 1130
     ||||||||||  ||  || ||  || || | |||||  |||||  ||  |
1006 TGCCAGTGGATCGACATCACCGACGTTAAACCGGGTAACTACATCCTGAA 1055

1131 GGTCAGTGTAAACCCCAGCTACCTGGTTCCTGAATCTGACTATACCAACA 1180
     |||  || || ||||||||| || || | ||||||| ||||| ||||||
1056 AGTTTCCGTTAACCCGTCCTACCTGGTTCCGGAATCCGACTACACCAACA 1105

1181 ATGTTGTGCGCTGTGACATTCGCTACACAGGACATCATGCGTATGCCTCA 1230
     | |||| ||  || || || ||| |||| || || || || |||| ||
1106 ACGTTGTTCGTTGCGATATCCGTTACACCGGTCACCACGCTTACGCTTCC 1155

1231 GGCTGCACAATTTCACCGTAT 1251
     || ||||||| || || |||
1156 GGTTGCACCATCTCCCCGTAC 1176
```

Fig. 3(2)

BLOCK 1: Coding strand

Oligo 1
GATCCCAGCAGCAGCCGCCGCGTGAACCGCCGGCTGCTCCGGGTGCTTGGCGTCAGCAGA-
TCCAGTGGGAAAACAACGGTCAGGTTTTCTCCCTG     (SEQ ID NO: 5)

Oligo 2
pCTGTCCCTGGGTTCCCAGTACCAGCCGCAGCGTCGTCGTGACCCGGGTGCTGCTGTTCC-
GGGTGCTGCTAACGCTTCCGCTCAGC     (SEQ ID NO: 6)

Oligo 3
pAGCCGCGTACCCCGATCCTGCTGATCCGTGACAACCGTACCGCGGCCGCTCGTACCCGT-
ACCGCTGGTTCCTCCGGTGTTACTGCA     (SEQ ID NO: 7)

BLOCK 2: Coding strand

Oligo 4
GGTCGTCCGCGTCCGACCGCGCGCCACTGGTTCCAGGCTGGTTACTCCACCTCCCGTGCT-
CGTGAAGCTGGTGCTTCCCGTGCTGAAAACCAG     (SEQ ID NO: 8)

Oligo 5
pACCGCTCCGGGTGAAGTTCCAGCGCTGTCCAACCTGCGTCCGCCGTCCCGTGTTGACGG-
TATGGTTGGTGACGACCCGTACAACCCGTACA     (SEQ ID NO: 9)

Oligo 6
pAGTACTCCGACGACAACCCGTACTACAACTACTACGACACCTACGAGCGCCCGCGTCCG-
GGTGGTCGTTACCGTCCGGGTTACGGTAC     (SEQ ID NO: 10)

BLOCK 3: Coding strand

Oligo 7
CGGTTACTTCCAGTACGGTCTGCCGGACCTGGTTGCTGACCCGTACTACATCCAGGCTTC-
CACCTACGTTCAGAAAATGTCCATGTAC     (SEQ ID NO: 11)

Oligo 8
pAACCTGCGTTGCGCTGCTGAAGAAAACTGCCTGGCTTCCACCGCTTACCGTGCTGACGT-
TCGTGACTACGACCACCGTGTTCTGCTGCGTTTCCCGC     (SEQ ID NO: 12)

Fig. 4(1)

Oligo 9
pAGCGTGTTAAAAACCAGGGCACCTCCGACTTCCTGCCGTCCCGTCCGCGTTACTCCTGG-
GAATGGCACTCCTGCCACCAGCACTACCACTCCATGGACG          (SEQ ID NO: 13)

BLOCK 4: Coding strand
Oligo 10
AATTCTCCCACTACGACCTGCTGGACGCTAACACCCAGCGTCGTGTTGCTGAAGGTCACA-
AAGCTTCCTTCTGCCTGGAAGACACCTCCTGCGACTACG          (SEQ ID NO: 14)

Oligo 11
pGTTACCACCGTCGTTTCGCTTGCACCGCTCACACCCAGGGTCTGTCCCCGGGTTGCTAC-
GACACCTACGGTGCTGACATCGACTGCCAGTGGA          (SEQ ID NO: 15)

Oligo 12
pTCGACATCACCGACGTTAAACCGGGTAACTACATCCTGAAAGTTTCCGTTAACCCGTCC-
TACCTGGTTCCGGAATCCGACTACACCAACAACG          (SEQ ID NO: 16)

Oligo 13
pTGGTTCGTTGCGATATCCGTTACACCGGTCACCACGCTTACGCTTCCGGTTGCACCATC-
TCCCCGTACTAATGATAG          (SEQ ID NO: 17)

COMPLEMENTARY OLIGONUCLEOTIDES
BLOCK 1: Complementary strand
Complementary to oligo 1
pGAAAACCTGACCGTTGTTTTCCCACTGGATCTGCTGACGCCAAGCACCCGGAGCAGCCG-
GCGGTTCACGCGGCGGCTGCTGCTGG          (SEQ ID NO: 18)

Complementary to oligo 2
pCGGAAGCGTTAGCAGCACCCGGAACAGCAGCACCCGGGTCACGACGACGCTGCGGCTGG-
TACTGGGAACCCAGGGACAGCAGGGA          (SEQ ID NO: 19)

Fig. 4(2)

Complementary to oligo 3
GTAACACCGGAGGAACCAGCGGTACGGGTACGAGCGGCCGCGGTACGGTTGTCACGGATC-
AGCAGGATCGGGGTACGCGGCTGCTGAG (SEQ ID NO: 20)

BLOCK 2: Complementary strand
Complementary to oligo 4
pTTCAGCACGGGAAGCACCAGCTTCACGAGCACGGGAGGTGGAGTAACCAGCCTGGAACC-
AGTGGCGCGCGGTCGGACGCGGACGACCTGCA (SEQ ID NO: 21)

Complementary to oligo 5
pGTTGTACGGGTCGTCACCAACCATACCGTCAACACGGGACGGCGGACGCAGGTTGGACA-
GCGCTGGAACTTCACCCGGAGCGGTCTGGTT (SEQ ID NO: 22)

Complementary to oligo 6
CGTAACCCGGACGGTAACGACCACCCGGACGCGGGCGCTCGTAGGTGTCGTAGTAGTTGT-
AGTACGGGTTGTCGTCGGAGTACTTGTACGG (SEQ ID NO: 23)

BLOCK 3: Complementary strand
Complementary to oligo 7
pGCAGGTTGTACATGGACATTTTCTGAACGTAGGTGGAAGCCTGGATGTAGTACGGGTCA-
GCAACCAGGTCCGGCAGACCGTACTGGAAGTACCGGTAC (SEQ ID NO: 24)

Complementary to oligo 8
pACACGCTGCGGGAAACGCAGCAGAACACGGTGGTCGTAGTCACGAACGTCAGCACGGTA-
AGCGGTGGAAGCCAGGCAGTTTTCTTCAGCAGCGCAAC (SEQ ID NO: 25)

Complementary to oligo 9
AATTCGTCCATGGAGTGGTAGTGCTGGTGGCAGGAGTGCCATTCCCAGGAGTAACGCGGA-
CGGGACGGCAGGAAGTCGGAGGTGCCCTGGTTTTTA (SEQ ID NO: 26)

Fig. 4(3)

BLOCK 4: Complementary strand
Complementary to oligo 10
pGCAGGAGGTGTCTTCCAGGCAGAAGGAAGCTTTGTGACCTTCAGCAACACGACGCTGGG-
TGTTAGCGTCCAGCAGGTCGTAGTGGGAG          (SEQ ID NO: 27)

Complementary to oligo 11
pGGCAGTCGATGTCAGCACCGTAGGTGTCGTAGCAACCCGGGGACAGACCCTGGGTGTGA-
GCGGTGCAAGCGAAACGACGGTGGTAACCGTAGTC          (SEQ ID NO: 28)

Complementary to oligo 12
pTGGTGTAGTCGGATTCCGGAACCAGGTAGGACGGGTTAACGGAAACTTTCAGGATGTAG-
TTACCCGGTTTAACGTCGGTGATGTCGATCCACT          (SEQ ID NO: 29)

Complementary to oligo 13
GATCCTATCATTAGTACGGGGAGATGGTGCAACCGGAAGCGTAAGCGTGGTGACCGGTGT-
AACGGATATCGCAACGAACCACGTTGT          (SEQ ID NO: 30)

Fig. 4(4)

SYNTHETIC POLYNUCLEOTIDES

This application is a 371 of PCT/AU97/00505 filed Aug. 11, 1997.

TECHNICAL FIELD

The present invention relates to synthetic polynucleotides encoding proteins and polypeptides selected from the group consisting of lysyl oxidases, lysyl oxidase-like proteins and variants thereof; to use of the synthetic polynucleotides to provide high yields of those proteins and polypeptides; and to uses of the proteins and polypeptides produced from the synthetic polynucleotides.

BACKGROUND ART

Lysyl oxidase is a copper dependent amine oxidase that catalyses the oxidation of amines, including but not limited to primary amines and, in particular, the amine side chain of lysine. Lysine oxidation catalysed by lysyl oxidase has been observed in the oligopeptide and polypeptide chains of collagen and tropoelastin. Lysyl oxidase activity has been observed with other amine containing substrates, such as oligopeptides where the efficiency of catalyzed oxidation is dependent on adjacent sequences (Kagan et al., 1995a) such as vicinal dicarboxylic amino acid residues (Nagan and Kagan, 1994).

With varying efficiencies, lysyl oxidases can oxidise other substrates, such as butylamine and p-hydroxybenzylamine, for example, to form butyraldehyde and p-hydroxybenzylaldehyde respectively. Non-peptide reactivity is also displayed with, for example, semi-carbazide(s) and oxidation of tyramine (Palcic et al., 1995). Lysyl oxidase activity has also been observed with other amine containing molecules including inhibitors and unnatural substrates such as trans-2-phenylcyclopropylamine (Shah et al., 1993).

The majority of the work done to date in characterising lysyl oxidase has been with respect to non-human mammalian lysyl oxidases. The level of amino acid homology between lysyl oxidases from different species is of the order of 90%.

"Lysyl oxidase-like proteins" have also been identified by the analysis of nucleotide and predicted amino acid sequence alignments of DNA and protein molecules which are expressed in a particular mammalian species including humans. The level of homology between these proteins and lysyl oxidases is of the order of 75%, which is a highly significant degree of homology. Evidence indicates that these molecules may function as enzymes in the extracelluar space as members of a lysyl oxidase family of molecules, and in the cell to provide lysyl oxidase activities (Kim, Y. et al. 1995).

The lysyl oxidase gene encodes a single polypeptide species and there has been no observation of lysyl oxidase mRNA splice variants or isoforms of the lysyl oxidase polypeptide in vivo (Boyd et al., 1995).

In the production of intra- and inter-molecular crosslinked molecules, lysine oxidation in tropoelastin is a necessary step in the formation of allysine, desmosine and isodesmosine condensation products.

Crosslinked molecules, including elastin and collagen, are significant components of fully functional connective tissue. In this regard, deficiencies in lysyl oxidase such as that found in lathyrism, lead to marked phenotypic changes that can compromise the viability of an individual.

Lysyl oxidase exists in at least two forms: an intracellular protein and the more thoroughly characterised extracellular form. In the intracellular form its roles include a ras recission function, and the encoding gene has been classified in this context as a ras-recission gene or rrg (Contente et al., 1990; Kenyon et al., 1991). In its capacity as rrg, its expression is altered in an incompletely catalogued manner, to apparently reduce the oncogenic phenotype of cells expressing aberrant ras. Lysyl oxidase levels also change during differentiation and development (Dimaculangan et al., 1994) and in response to growth factors (Green et al, 1995). Lysyl oxidase is also a secreted protein, available in the extracellular matrix of some connective tissues in very low concentrations.

Difficulties in obtaining sufficient quantities of enzyme for biochemical analysis have impeded detailed exploration of its properties. Yields of purified naturally occurring lysyl oxidase available from typical purification procedures have been limited to 2–4 mg starting with 0.5 to 1 kg of cleaned bovine aortae (Kagan and Cai, 1995).

Extracellular lysyl oxidase is typically made as a larger protein, which includes a collection of amino acid residues at the amino terminus of the protein. This form, termed preprolysyl oxidase is secreted from the cell in a process contemporaneous with cleavage of the amino-terminal region to generate prolysyl oxidase which in turn is cleaved outside the cell to generate the mature form of the protein.

The extracellular (and possibly intracellular) lysyl oxidase enzyme additionally contains copper and at least one organic cofactor which is postulated to be a quinone-like component. The organic cofactor has variously been considered to be covalently or non-covalently bound to the enzyme (Williamson et al., 1986; Kagan and Trackman, 1991). Examples of organic cofactors, which have been found to be associated with oxidases, include quinones such as P.Q.Q., topa quinone (2,4,5 trihydroxyphenylalanine quinone) and tryptophan tryptophylquinone (Tanizawa, 1995). The organic cofactor for lysyl oxidase is now known to be a quinone. It is possible that the cofactor can be supplied, generated by interaction of a quinone derivative with the depleted apo-form of the enzyme, and/or generated by protein oxidation such as that mediated by the participation of copper. There is at least one atom of copper tightly bound per one molecule of functional enzyme. However it was experimentally demonstrated (Gacheru et al., 1990) that when copper is removed by a chelating agent the inactive apoenzyme can be restored to its former level of activity by the addition of copper.

Posttranslational modification(s) such as glycosylation have not been described for the mature form of lysyl oxidase, although there is evidence for glycosylation of the amino terminal region destined for removal during maturation of the precursor prolysyl oxidase (Cronshaw et al., 1995). As other forms of modification exist in vertebrate cells, and include participation by the cytosol, Golgi and secretion machinery, followed by extracellular processing, uncertainty has surrounded the question of whether a functional lysyl oxidase could be made in host cells other than verterbrate systems.

Isolation of endogenous lysyl oxidase from, for example, mammalian tissue typically uses chemical agents which interfere with protein association, such as urea. Modest amounts of lysyl oxidase can be recovered in this way from skin (Shackleton and Hulmes, 1990). The purified material is typically maintained in solutions containing chemical agent(s), in part to minimise protein aggregation and loss of catalytic function. When prepared in this way, the enzyme displays sluggish activity, which has led to the assertion that the enzyme (or a macromolecular complex) (Cronshaw et al.,1993) is altered during the relatively harsh extraction procedure (Shackleton and Hulmes, 1990).

To circumvent difficulties associated with the use of the purified naturally occurring enzyme, recombinant production is a logical alternative. However despite the fact that inferred lysyl oxidase sequences including human (Mariani et al., 1992; Svinarich et al., 1992; Kenyon et al., 1993), rat (Trackman et al., 1990) and mouse (Contente et al., 1993) have been available for several years there have been no reports in the literature of production of recombinant functional lysyl oxidase using non-mammalian hosts for other than modest levels of expression and no functional expression of the human sequence. Kagan et al. (1995b), have reported the production of modest levels of porcine lysyl oxidase from cDNA in mammalian cells indicating that bacterial production of functional enzyme was problematic. One of the impediments to the production of recombinant lysyl oxidase has been the discrepancies appearing in some of the available sequence information (e.g. Trackman et al., 1990; Hamalainen et al., 1991 vs Mariani et al., 1992).

DESCRIPTION OF THE INVENTION

The paucity of information in the literature in relation to the nature of host-specific post-translational modifications of lysyl oxidase (e.g. Cronshaw et al. 1995), together with the real absence of reports of functional lysyl oxidase production in non-mammalian recombinant expression systems, teaches against the choice of non-mammalian hosts for expression of nucleotide sequences encoding mammalian lysyl oxidase and implies that non-mammalian host cells are unlikely to produce functional lysyl oxidase which is encoded by a mammalian nucleotide sequence.

The present inventor has reasoned that expression of mammalian lysyl oxidase in non-mammalian host cells might be achieved using a synthetic polynucleotide which encodes lysyl oxidase but which has been specifically designed for use in non-mammalian host cells such as (but not limited to) *Escherichia coli*, *Saccharomyces cerevisiae* and *Pichia*. In particular, the inventor proposed the hypothesis that non-mammalian host cells have difficulty expressing from nucleotide sequences encoding mammalian lysyl oxidase because of the presence of 'rare' codons in those sequences which are used infrequently in the non-mammalian host cell. Rare codons are codons that are found at low frequency in highly expressed genes in a particular host. A measure of efficiencies of codon usage is the codon adaptation index (CAI) (Sharp and Li 1987). Highly expressed genes such as those encoding ribosomal proteins in *E. coli* typically have high CAI values that are greater than or equal to 0.45, whilst poorly expressed genes have much smaller CAI values; for example, the *E. coli* lacI gene has a CAI of 0.3

The inventor calculated the CAI of a nucleotide sequence encoding a secreted form of human lysyl oxidase for a number of non-mammalian hosts by considering the usage of codons in the nucleotide sequence shown in FIG. 1. The CAI is calculated to be 0.24 for *E. coli* and 0.11 for *Saccharomyces cerevisiae*. The inventor identified codons in the nucleotide sequence encoding human lysyl oxidase which are infrequently used in host cells such as *E. coli* including: an AGGAGA cluster encoding adjacent arginine residues at positions 937 to 942 which has the capacity to limit expression and generate translational pausing and frameshifting in *E. coli*; 11 other instances of single rare AGG and AGA arginine codons capable of instigating translational hopping (Kane 1992); and an ensemble of codons rarely found in highly expressed *E. coli* genes (Table 1). Together these codons account for 28% of the amino acid coding capacity of the sequence.

TABLE 1

Codons found in the natural lysyl oxidase sequence of FIG.1 which are rarely found in highly expressed *E. coli* genes

| Codon | Amino acid | Frequency in highly expressed genes % | Occurrence in FIG. 1 residues (% total sequence) |
|---|---|---|---|
| AGG | Arg | 0.14 | 6    2.4 |
| AGA | Arg | 0.21 | 7    2.8 |
| CGA | Arg | 0.31 | 2    0.8 |
| CCC | Pro | 0.43 | 7    2.8 |
| TGT | Cys | 0.47 | 7    2.8 |
| TGC | Cys | 0.61 | 3    1.2 |
| ACA | Thr | 0.65 | 7    2.8 |
| CCT | Pro | 0.66 | 6    2.4 |
| TCA | Ser | 0.68 | 3    1.2 |
| GGA | Gly | 0.70 | 4    1.6 |
| AGT | Ser | 0.72 | 6    2.4 |
| CCA | Pro | 0.82 | 2    0.8 |
| TCC | Ser | 0.94 | 4    1.2 |
| GGG | Gly | 0.97 | 2    0.8 |
| CTG | Leu | 0.99 | 6    2.4 |

In consideration of the CAI values for the nucleotide sequence encoding human lysyl oxidase in *E. coli* and *Saccharomyces cerevisiae*, the inventor reasoned that the problem associated with expression of verterbrate lysyl oxidase or lysyl oxidase-like molecules in particular host cells or expression systems was directly related to the high proportion of codons in the verterbrate lysyl oxidase or lysyl oxidase-like protein nucleotide sequence which are rarely used by the particular host cells. The inventor further reasoned that verterbrate lysyl oxidase and lysyl oxidase-like molecules might be expressed in alternative host cells if the nucleotide sequences encoding those molecules were able to be specifically designed so as to favour higher levels of expression of lysyl oxidase in a particular alternative host cell. The inventor reasoned that nucleotide sequences which encode verterbrate lysyl oxidase or lysyl oxidase-like proteins and which have been specifically designed for high level expression in a particular host may also be suitable for expression in other host cells provided that the specifically designed nucleotide sequence contained codons which were frequently used by the other host cells. Moreover, the inventor realised that the concept of modifying the nucleotide sequence would find application in producing high level expression of lysyl oxidase or lysyl oxidase-like proteins in the natural host cell, in particular, high level expression of nucleotide sequences encoding human lysyl oxidase and lysyl oxidase-like proteins in human cells.

The present invention provides high level expression of nucleotide sequences encoding lysyl oxidases and lysyl oxidase-like proteins in recombinant expression systems. The inventor has recognised that lysyl oxidases, lysyl oxidase-like proteins and variants thereof can be used in a variety of, for instance, pharmaceutical applications, but these uses require significant quantities of lysyl oxidase, lysyl oxidase-like proteins or variants thereof in a native conformation. Thus the realisation of the potential application of lysyl oxidase, lysyl oxidase-like expression products and variants thereof first requires a system which allows high level production of those products in native conformation.

The benefits of being able to produce significant amounts of expression product in a functional conformation include specific oxidation, rather than random oxidation, so as to produce cross-linked complexes including cross-linked elastin or cross-linked collagen which are structurally and functionally similar to normal physiological complexes.

Secondly, the expression product which exists in a functional or native conformation is unlikely to cause an adverse reaction in vivo, whether the expression product is directly administered in vivo or in the situation where residual expression product remains in a cross-linked complex after catalysis, wherein that complex is intended for in vivo use.

The invention provides for high level expression of vertebrate nucleotide sequences encoding lysyl oxidase and lysyl oxidase-like proteins by generating synthetic polynucleotides which encode lysyl oxidase or lysyl oxidase-like proteins. Synthetic polynucleotides are nucleotide sequences which have been specifically designed for high level expression of lysyl oxidase or lysyl oxidase-like proteins in particular host cells.

Synthetic polynucleotides of the invention are generated by introducing specific nucleotide mutations at specific positions with respect to a particular codon, so as to replace codons which are rarely used, with codons which are frequently used by the particular host. Typically the mutation will not encode an amino acid mutation. To this extent, the nucleotide mutations within the synthetic polynucleotide are silent mutations. The number of codons corresponding to each amino acid residue is shown in Table 2. As a result of the degeneracy of the genetic code it is recognised that for some amino acid residues, silent mutations may be introduced at any one of nucleotide positions 1, 2 or 3 of a particular codon. It is further recognised that for some amino acid residues, for example cysteine, arginine, glutamine, few silent mutations may be introduced. In particular methionine and tryptophan residues are both generally encoded by a single codon. Nonetheless, the present inventor anticipates that, as a result of the known low stringency codon-anticodon interaction at nucleotide position 3 which gives rise to the "wobble effect", (Crick, F. et al. 1966) further silent mutations may be introduced at position 3, so as to increase the number of codons for a particular amino acid residue which may be selected by a particular host cell.

| | | The Genetic Code | | | |
|---|---|---|---|---|---|
| First Position | | Second Position | | | Third Position |
| (5' end) | U | C | A | G | (3' end) |
| U | PHE | SER | TYR | CYS | U |
| | PHE | SER | TYR | CYS | C |
| | LEU | SER | Stop | Stop | A |
| | LEU | SER | Stop | TRP | G |
| C | LEU | PRO | HIS | ARG | U |
| | LEU | PRO | HIS | ARG | C |
| | LEU | PRO | GLN | ARG | A |
| | LEU | PRO | GLN | ARG | G |
| A | ILE | THR | ASN | SER | U |
| | ILE | THR | ASN | SER | C |
| | ILE | THR | LYS | ARG | A |
| | MET | THR | LYS | ARG | G |
| G | VAL | ALA | ASP | GLY | U |
| | VAL | ALA | ASP | GLY | C |
| | VAL | ALA | GLU | GLY | A |
| | VAL | ALA | GLU | GLY | G |

Note:
Given the position of the bases in a codon, it is possible to find the corresponding amino acid. For example, the codon (5')AUG(3') on mRNA specifies methionine, whereas CAU specifies histidine. UAA, UAG and UGA are termination signals. AUG is part of the initiation signal, and it codes for internal methionines as well.

The present invention also relates to synthetic polynucleotides encoding lysyl oxidase or lysyl oxidase-like proteins wherein the nucleotide sequence of the synthetic polynucleotide comprises mutations which encode amino acid mutations. The lysyl oxidase and lysyl oxidase-like proteins which contain amino acid sequence mutations are variants of lysyl oxidase or lysyl oxidase-like proteins and are also described herein as variants of the invention. As described below, variants of the invention retain the functional properties of lysyl oxidase and lysyl oxidase-like proteins, namely that they catalyse oxidation of amine groups including lysine. The amino acid sequence of lysyl oxidase or lysyl oxidase-like proteins may be mutated by addition, deletion, substitution or combinations thereof of the encoding nucleotide sequence and such altered molecules are variants of the invention provided they retain the required activity. In particular, the inventor has recognised that the amino acid sequence of lysyl oxidase or lysyl oxidase-like proteins may be altered without significantly changing the specificity or efficacy of the enzyme, so that the enzyme containing the amino acid mutation is substantially the same as the enzyme comprising the native amino acid sequence. The inventor also recognises that the specific activity and substrate specificity may be altered by mutation of lysyl oxidase or lysyl oxidase-like protein amino acid sequence.

Thus the present invention further provides amino acid sequence variants of lysyl oxidase and lysyl oxidase-like proteins. Variants of the invention retain the functional properties of lysyl oxidase and lysyl oxidase-like proteins, namely that they catalyse oxidation of amine groups including lysine. Variants of the invention have amino acid sequences which are homologous with the amino acid sequence of lysyl oxidase or lysyl oxidase-like proteins. For the purposes of this description, "homology" between the amino acid sequence of a lysyl oxidase or lysyl oxidase-like protein and that of a variant connotes a likeness short of identity, indicative of a derivation of one sequence from the other. In particular, an amino acid sequence is homologous to that of a lysyl oxidase or lysyl oxidase-like protein if the alignment of that amino acid sequence with the sequence of a lysyl oxidase or a lysyl oxidase-like protein reveals a similarity of about 65% over any 20 amino acid stretch or over any repetitive element of the molecules shorter than 20 amino acids in length. Such a sequence comparison can be performed via known algorithims such as the one described by Lipman and Pearson (1985), which are readily implemented by computer. Similarity is observed between amino acids where those amino acids have a side chain which confers a similar chemical property in the same chemical environment. For example, threonine and serine are similar amino acids; aspartic acid and glutamic acid are similar amino acids; valine, leucine and isoleucine are similar amino acids etc. Thus an amino acid sequence may be considered homologous with the amino acid sequence of a lysyl oxidase or a lysyl oxidase-like protein because the alignment of those sequences reveals a similarity of 65%, although at each amino acid position in the aligned sequences, none of the residues are identical.

According to a first aspect of the present invention, there is provided a synthetic polynucleotide encoding an amino acid sequence selected from the group consisting of lysyl oxidases, lysyl oxidase-like proteins and variants thereof.

The lysyl oxidase may be a vertebrate including human, bovine, porcine, rat or mouse lysyl oxidase, or avian lysyl oxidase including chick lysyl oxidase. Preferably, the lysyl oxidase is a human lysyl oxidase. The nucleotide sequences of rat and mouse lysyl oxidase are reported in Trackman et al. (1991), porcine in Cronshaw et al. (1993), mouse in Contente et al. (1993), and chick in Wu et al. (1992).

The lysyl oxidase-like proteins of the present invention are proteins which exhibit an amine oxidation catalysing function.

The variants of lysyl oxidases and lysyl oxidase-like proteins in accordance with the present invention may be truncated forms of the lysyl oxidase or lysyl oxidase-like proteins wherein the truncated forms retain the functional properties of lysyl oxidase and lysyl oxidase-like proteins, in particular the ability to catalyse the oxidation of amine groups, including lysine. In toto, the truncated forms are typically greater than 20 amino acids in length.

The variants of the invention also include molecules that comprise a particular sequence of amino acids or a particular domain of a lysyl oxidase or lysyl oxidase-like protein wherein the sequence of amino acids or domain retain the functional properties of lysyl oxidase and lysyl oxidase-like proteins, in particular the ability to catalyse the oxidation of amine groups, including lysine.

Synthetic polynucleotides according to the invention are generated by mutating the native nucleotide sequence encoding a lysyl oxidase or lysyl oxidase-like protein or variant so that:

a) all or some of the codons which hamper expression in the expression system in which the polynucleotide is to be expressed, are replaced with codons more favourable for expression in the expression system; and b) the altered sequence encodes a protein or polypeptide selected from the group consisting of lysyl oxidases, lysyl oxidase-like proteins and variants thereof.

In one preferred embodiment the synthetic polynucleotide comprises a nucleotide sequence which encodes lysyl oxidase wherein the nucleotide sequence has a CAI score of at least 0.3 in a particular host cell. More preferably the synthetic polynucleotide comprises a nucleotide sequence which encodes human lysyl oxidase, wherein the synthetic polynucleotide has a CAI of at least 0.3 in *E. coli*. Most preferably the synthetic polynucleotide comprises all or part of the nucleotide sequence shown in FIG. 2 (SEQ ID NO:3), starting at residue 141 (Met) or 144(Asp). In the sequence shown in FIG. 2 (SEQ ID NO :3) the N-terminal encoded amino acid is serine. The presence of the serine residue is the consequence of the insertion of a BamHI restriction site at this position. It will be readily recognised that this serine residue could be deleted or replaced by an alternative residue related to the restriction site present at the N-terminal end of the construct. Similarly, at the 3' end of the construct, additional stop codons are inserted compared to the parent sequence shown in FIG. 1 (SEQ ID NO: 1). These stop codons are a feature of this particular construct.

With respect to the sequence of the lysyl oxidase molecule, the first 21 amino acids of the sequence shown in FIG. 1 (SEQ ID NO:2) are amino acids of the pre-sequence. The residues from this position and up to and including residue 143 comprise the pro-sequence. Thus the mature form of the. lysyl oxidase commences at residue 144. These different constructs are encompassed within the synthetic polynucleotides and encoded products of the invention.

In another preferred embodiment, at least 50% of codons in a particular nucleotide sequence which may be altered so as to reflect frequent codon usage in a particular host, are selected and altered. More preferably at least 60% are altered. Most preferably at least 70% are altered.

In another preferred embodiment at least 50% of codons which encode a particular amino acid are altered, so as to reflect frequent codon usage in a particualar host. More preferably at least 60% are altered. Most preferably at least 70% are altered.

Modifications to codon usage to provide enhanced expression for a variety of hosts are discussed in: Zhang et al. (1991), for *E. coli*, yeast, fruit fly and primates where codon usage tables are provided; Newgard et al. (1986), for mammals; and Murray et al. (1989), for plants. Preferred codon usages are indicated in these publications.

It is important to recognise that even where human originating nucleotide sequences are to be expressed in human cell lines, or other mammalian cell lines, that modifications to codon usage can still be beneficial to producing enhanced levels of the protein of interest. The same applies to expression of other lysyl oxidase and lysyl oxidase like proteins in cell lines derived from their originating species or other mammalian or avian species.

In another preferred embodiment, all or part of the 5' or 3' untranslated region, or intronic regions of the synthetic nucleotide sequence encoding the lysyl oxidase or lysyl oxidase-like protein or variant thereof, are deleted.

In another preferred embodiment, all or part of the regions encoding the signal peptide, or regions encoding the pro-peptide, of the synthetic nucleotide sequence encoding the lysyl oxidase or lysyl oxidase-like protein or variant thereof, are deleted.

More preferably, all or part, of the 5' or 3' untranslated region, and/or intronic regions, and regions encoding the signal peptide, and/or regions encoding the pro-peptide, of the synthetic polynucleotide encoding the lysyl oxidase or lysyl oxidase-like protein or variant thereof are deleted.

It will be recognised that the strategies for specific synthetic gene construction to yield enhanced expression of lysyl oxidases described in detail herein, can readily be adapted to the synthesis of other lysyl oxidases, lysyl oxidase-like proteins and variants thereof not specifically exemplified here, in light of the significant degree of homology between these molecules and in light of the fact that the present inventor has established that these proteins can be expressed in functional form in significant amounts from particular host cells using synthetic gene constructs with enhanced codon usage.

In another preferred embodiment the synthetic polynucleotide comprises a nucleotide sequence encoding lysyl oxidase, lysyl oxidase-like protein or a variant thereof and a further nucleotide sequence, wherein the nucleotide sequence encoding lysyl oxidase, lysyl oxidase-like protein or a variant thereof and the further nucleotide sequence are chemically linked so as to encode a single open reading frame. The further nucleotide sequence is preferably chemically linked to the 5' end of the nucleotide sequence encoding lysyl oxidase, lysyl oxidase-like protein or a variant thereof.

In another preferred embodiment, the further nucleotide sequence encodes all of part of a polypeptide which causes the lysyl oxidase, lysyl oxidase-like protein or variant thereof to be either secreted to the extracellular environment, expressed as a cell surface periplasmic protein, or expressed in the intracellular environment. Preferably the further nucleotide sequence encodes all or part of glutathione S-transferase.

In another preferred embodiment the further nucleotide sequence encodes additional residues such as an N-terminal methionine or formyl-methionine.

In a preferred form of the invention the synthetic polynucleotide is unfused.

In another preferred embodiment, the synthetic polynucleotide comprises a fragment of the nucleotide sequence shown in FIG. 2, wherein the fragment of the nucleotide sequence encodes a protein which retains the enzymatic activity of lysyl oxidase, lysyl oxidase-like protein or a variant thereof. Preferably the synthetic polynucleotide comprises the sequence shown in FIG. 2 and commencing at the codon encoding residue 141. In another preferred embodiment the synthetic polynucleotide comprises the sequence shown in FIG. 2 and commences at or near the codon encoding residue 144.

In a further preferred embodiment, the synthetic polynucleotide comprises the nucleotide sequence shown in FIG. 2 (SEQ ID NO:3), or a fragment thereof, in which only some of the nucleotide mutations have been introduced. Preferably, the synthetic polynucleotide comprises the nucleotide sequence shown in FIG. 2 (SEQ ID NO:3), or a fragment thereof, and at least 50% of the nucleotide mutations have been introduced. More preferably, the synthetic polynucleotide comprises the nucleotide sequence shown in FIG. 2 (SEQ ID NO:3) in which the number of nucleotide mutations which have been introduced produce a CAI score for the synthetic polynucleotide in *E. coli* of at least 0.30.

The production of the synthetic polynucleotides of the invention, which is described in detail in the accompanying Examples, can be via the techniques of organic synthesis or recombinant DNA technology, or a combination of both techniques.

The synthetic polynucleotides described in the accompanying Examples were designed to make them amenable to cloning and expression in fused and unfused forms, and for intracellular and secreted production.

Where the synthetic polynucleotide is prepared from assembled oligonucleotides it is preferred to incorporate restriction sites in the sequence to facilitate assembly of the polynucleotide.

Restriction sites incorporated in the polynucleotide sequence are also useful for:
1. facilitating subcloning of manageable blocks for sequence confirmation;
2. providing sites for later introduction of modifications to the polynucleotide as insertions, deletions or base changes;
3. facilitating confirmation of correct poly-nucleotide assembly by restriction endonuclease digestion.

The synthetic polynucleotides encoding the variants of the invention can be produced by the techniques of site-directed mutagenesis or random mutagenesis. These techniques allow one to determine the effect of mutation at particular positions in the synthetic polynucleotide sequence on the amine oxidation catalysing properties of the encoded variant of the invention.

In one preferred embodiment, the variants of the invention are produced by the technique of site-directed mutagenesis using oligonucleotides, which comprises the following steps:
1. synthesis of an oligonucleotide with a sequence that contains the desired nucleotide mutation;
2. hybridizing the oligonucleotide to a template nucleotide sequence encoding lysyl oxidase or a lysyl oxidase-like protein; and
3. using a DNA polymerase to extend from the 3' end of the oligonucleotide in the 5' to 3' direction.

Another approach which is particularly suited to situations where the synthetic polynucleotide has been prepared from oligonucleotide blocks bounded by restriction sites is cassette mutagenesis where entire restriction fragments are inserted, deleted or replaced.

According to a second aspect of the present invention there is provided a recombinant nucleic acid molecule comprising a synthetic polynucleotide of the first aspect. Preferably the recombinant nucleic acid molecule comprises vector nucleic acid.

The vectors of the invention include plasmids, phages, and phagemids. The vectors of the invention can be used in integrative expression systems or lytic or comparable expression systems.

Suitable vectors will generally contain origins of replication and control sequences which are derived from species compatible with the intended expression host. Typically these vectors include a promoter located upstream from the synthetic polynucleotide, together with a ribosome binding site if intended for prokaryotic expression, and a phenotypic selection gene such as one conferring antibiotic resistance or supplying an auxotrophic requirement. For production vectors, vectors which provide for enhanced stability through partitioning may be chosen. Where integrative vectors are used it is not necessary for the vector to have an origin of replication. Lytic and other comparable expression systems do not need to have those functions required for maintenance of vectors in hosts.

For *E. coli* typical vectors include pBR322, pBluescript II SK+, PGEX-2T, pTrc99A, pET series vectors, particularly pET3d, (Studier et al. 1990) and derivatives of these vectors.

In one preferred embodiment, the vector comprises a synthetic polynucleotide of the first aspect, wherein the synthetic polynucleotide has a CAI score of at least 0.30 in a particular host cell. Preferably the vector comprises all or part of a synthetic polynucleotide sequence shown in FIG. 2 (SEQ ID NO:3).

In another preferred embodiment, the vector comprises a synthetic polynucleotide of the first aspect wherein at least 50% of codons in a particular nucleotide sequence which may be altered so as to reflect frequent codon usage in a particular host, are selected and altered. More preferably at least 60% are altered. Most preferably at least 70% are altered.

In another preferred embodiment the vector comprises a synthetic polynucleotide of the first aspect wherein at least 50% of codons which encode a particular amino acid are altered, so as to reflect frequent codon usage in a particular host. More preferably at least 60% are altered. Most preferably at least 70% are altered.

In another preferred embodiment the vector comprises a synthetic polynucleotide of the first aspect wherein all or part of the 5' or 3' untranslated region, and/or intronic regions is deleted.

In another preferred embodiment the vector comprises a synthetic polynucleotide of the first aspect wherein all or part of the regions encoding the signal peptide, and/or regions encoding the pro-peptide is deleted.

In another preferred embodiment the vector comprises a synthetic polynucleotide of the first aspect wherein all or part, of the 5' or 3' untranslated region, and/or intronic regions, and/or all or part of the regions encoding the signal peptide, and or regions encoding the pro-peptide is deleted.

In another preferred embodiment, the recombinant DNA molecule comprises a synthetic polynucleotide of the first aspect, wherein the synthetic polynucleotide sequence is chemically linked to a further nucleotide sequence so as to encode a single open reading frame for the synthetic polynucleotide and the further nucleotide sequence. Preferably, the recombinant DNA molecule comprises a synthetic polynucleotide and the further nucleotide sequence wherein the further nucleotide sequence is chemically linked to the 5' end of the synthetic polynucleotide.

In another preferred embodiment, the recombinant DNA molecule comprises a synthetic polynucleotide, wherein the synthetic polynucleotide comprises all or part of the nucleotide sequence shown in FIG. 2 (SEQ ID NO:2). Preferably, the recombinant DNA molecule comprises a synthetic polynucleotide sequence having all or part of the sequence shown in FIG. 2 (SEQ ID NO:3) wherein only some of the indicated nucleotide mutations have been introduced.

According to a third aspect of the present invention there is provided a host cell transformed with a recombinant DNA molecule of the second aspect of the invention.

The host cells may be prokaryotic cells including bacteria, and may also include yeasts, insect cells and other eukaryotic cells or whole organisms.

In a preferred embodiment, the host is an *E. coli* strain including *E. coli* B strain derivatives (Studier et al. 1990), and *E. coli* K12 derivatives such as NM522 (Gough and Murray, 1983) and XL1-Blue (Bullock et al. 1987).

In another preferred embodiment, the host is *S. cerivisiae* or Pichia.

According to a fourth aspect of the present invention there is provided an expression product, wherein the expression product is derived from a host cell of the third aspect, the expression product comprising an amino acid sequence selected from the group consisting of lysyl oxidase, lysyl oxidase-like proteins and variants thereof.

In one preferred embodiment, the expression product comprises the amino acid sequence shown in FIG. 2 (SEQ ID NO:4) and is encoded by a synthetic polynucleotide which comprises the nucleotide sequence shown in (SEQ ID NO:3).

In an alternative embodiment, the expression product comprises a fragment of the amino acid sequence shown in FIG. 2 (SEQ ID NO:4) which retains amine oxidation catalysing properties, and is encoded by a synthetic polynucleotide comprising the corresponding nucleotide sequence shown in FIG. 2 (SEQ ID NO:3). Preferably the expression product comprises an amino acid sequence having an N-terminus at amino acid residue position 141 (Met) of FIG. 2 (SEQ ID NO:4) or results in an N-terminal amino acid residue position 144 (Asp) of FIG. 2, (SEQ ID NO:4) and is encoded by a synthetic polynucleotide comprising the corresponding nucleotide sequence shown in FIG. 2 (SEQ ID NO:3).

In another preferred embodiment, the expression product is encoded by a synthetic polynucleotide comprising the nucleotide sequence shown in FIG. 2 (SEQ ID NO : 3) in which only some of the nucleotide mutations have been introduced. Preferably the expression product is encoded by a synthetic polynucleotide comprising all or part of the nucleotide sequence shown in FIG. 2 (SEQ ID NO:3) and at least 50% of the nucleotide mutations relative to FIG. 1 have been introduced. More preferably the expression product is encoded by a synthetic polynucleotide comprising all or part of the nucleotide sequence shown in FIG. 2 (SEQ ID NO:3) in which the number of nucleotide mutations which have been introduced produce a CAI score for the synthetic polynucleotide in *E. coli* of at least 0.30.

The expression products of the fourth aspect may be fused expression products which include all or part of a protein encoded by the vector in peptide linkage with the expression product. They may also include, for example, an N-terminal methionine or other additional residues which do not permanently impair the catalytic properties of the product.

In a further preferred embodiment, the expression products of the invention are fusion products which comprise an amino acid sequence selected from the group consisting of lysyl oxidase, lysyl oxidase-like proteins and variants thereof which are encoded by a synthetic polynucleotide, wherein the amino acid sequence is chemically linked to a further amino acid sequence. Typically, the further amino acid sequence is chemically linked to the N-terminus of the expression product. Preferably the further amino acid sequence allows purification of the fusion product. Most preferably the further amino acid sequence comprises an amino acid sequence encoding glutathione S-transferase. The further amino acid sequence may be chosen in order to cause the fusion product to be secreted to the extracellular evironment, expressed as a cell membrane protein or expressed in the intracellular environment.

The expressed fusion products may subsequently be treated to remove the further amino acid sequence from the amino acid sequence selected from the group consisting of lysyl oxidase, lysyl oxidase-like proteins and variants thereof. Preferably, the treatment is via chemical cleavage. In another more preferred embodiment, the treatment is via protease digestion. Still more preferably, the treatment is effected by endogenous host cell secretion machinery, for example yeast cell secretion machinery.

Non-fused systems include the introduction of or use of a pre-existing methionine codon. An example of this is the use of pET3a and pET3d in *E. coli*.

In a further embodiment, the invention provides a pharmaceutical composition comprising an expression product of the invention and a pharmaceutically acceptable carrier, excipient or diluent. The pharmaceutical compositions are prepared and tested according to standard pharmaceutical practise. The support for their efficacy is provided by the assays in the Examples.

According to a fifth aspect of the invention there is provided a method for producing an expression product of the invention, the method comprising the following steps:

(i) providing a host cell of the third aspect of the invention.

(ii) maintaining the host cell in conditions suitable for expression of the synthetic polynucleotide; and (iii) isolating the expression product.

In one preferred embodiment the expression product is produced by expression of the synthetic polynucleotide in *E. coli*. The invention extends to the use of other host cells which are capable of producing the expression product by expression of the synthetic polynucleotides designed for use in *E. coli*.

In another preferred embodiment, the expression product is produced by expression of a synthetic polynucleotide of the invention in other microbial expression systems including prokaryotic expression systems such as bacterial expression systems, and also including insect cell expression systems, and expression systems involving other eukaryotic cells or whole organisms. Again synthetic polynucleotides which are designed for use in a particular host can also be used in other cells which provide high expression of that sequence.

As disclosed in the Examples, the inventor has determined that it is useful to add Cu to the expression product which has been purified from the inclusion bodies of *E. coli* or similar organisms, so that the expression product can fold into a functional conformation which has the enzymatic activity of lysyl oxidase or lysyl oxidase-like proteins. The role of Cu in solubilising lysyl oxidase protein was not apparent until the present invention was carried out. Indeed based on earlier reported results which show that inactive apoenzyme can be reactivated by the addition of Cu it would have been expected that re-folding could occur without Cu. The present inventor initially attempted to refold protein in the absence of Cu and failed to generate soluble protein. It was only in subsequent experiments where Cu was added that refolding in this environment succeeded.

Further, should over expressed lysyl oxidase lack copper after its production in bacteria, the incorporation of copper into the recombinant protein would be possible by adapting the previously reported protocol (Gacheru et al. 1990) used for conversion of the apoenzyme of natural lysyl oxidase into the metal containing form.

In addition, it would be desirable to add oxidising substances that assist in the production of the organic cofactor if this is not formed by the enzyme under the prevailing conditions without assistance. The most important additional substance is oxygen in solution.

It is proposed here that generation of the active enzyme in vitro is a time-dependent process involving the introduction of copper to the overexpressed polypeptide, followed by oxidation of the protein to generate the covalently bound quinone. This is despite the absence of a Asn-Tyr-Asp/Glu consensus sequence from lysyl oxidase presumed to be important to this type of process (Tanizawa 1995).

The expression product may be exposed to chemical agents to enhance the stability and activity of the molecule. The chemical agents include various concentrations of urea or glycerol combined with storage at −20° C.

In one preferred form the expression product is produced in the form of inclusion bodies which are harvested from the transformed host.

As described above, the inventor recognised a variety of uses for lysyl oxidase, lysyl oxidase-like proteins and variants thereof although these uses require significant amounts of protein in functional conformation. As the inventor has for the first time produce significant amounts of enzyme in functional conformation, the following uses, as described below can now be realised.

The invention provides a method of cross-linking molecules that contain primary amines, wherein the molecules are associated with a cell membrane or extracellular environment, comprising contacting the primary amine with an expression product of the invention.

As described in the Examples, the inventor now recognises that the expression products of the invention have specific activity for primary amine groups in peptide and non-peptide substrates. Furthermore, as described in the Examples, as the present inventor has, for the first time, observed cross-linking of both peptide and non-peptide substrates in vitro, using the expression product of the invention, the inventor envisages that the expression products of the invention will be useful for cross-linking a wide range of molecules such as peptides and polypeptides, non-peptide chemical polymers which contain primary amine groups and combinations thereof. In particular, the present inventor envisages that the expression product of the invention will be widely applicable to methods of treatment in vivo, in particular where those methods of treatment require cross-linking of elastin or collagen. For this purpose the expression product can be formulated in suitable carriers, buffers and other conventional delivery systems.

In one preferred embodiment, the invention provides a method of cross-linking molecules that contain primary amines, wherein the molecule is a peptide or polypeptide molecule and the primary amine is associated with an amino acid side chain. The method comprises contacting the peptide or polypeptide molecule with an expression product of the invention under conditions suitable to cross-link the molecules. Preferably, the peptide or polypeptide comprises the amino acid sequence of tropoelastin or a fragment thereof. In another preferred embodiment, the peptide or polypeptide comprises the amino acid sequence of collagen or a fragment thereof. It can also comprise both.

In another preferred embodiment the invention provides a method of cross-linking molecules that contain primary amines, wherein the the molecule is a non-peptide molecule. The method comprises contacting the non-peptide molecule with an expression product of the invention under conditions suitable to cross-link the molecules.

The present inventor also recognises that the expression products of the invention would find wide application in accelerating the rate of wound healing. In particular the inventor has recognised that lysyl oxidase, lysyl oxidase-like proteins and variants thereof may be used to accelerate wound healing. Wound healing may be accelerated by administering an expression product of the invention to the wound. Alternatively, an expression product of the invention may be included in a matrix including an elastin, tropoelastin and/or collagen based or amine containing matrix which is itself applied to the wound. In both methods, wound healing is accelerated by cross-linking of molecules which contain primary amines, and the cross-linking is mediated by the expression product of the invention. For this purpose the expression product can be formulated in suitable carriers, buffers and other conventional delivery systems.

Thus the invention provides a method of accelerating the rate of wound healing, the method comprising the step of administering an expression product of the invention to a wound under conditions which are suitable for cross-linking of molecules containing primary amines. Preferably, an expression product of the invention is administered to the wound by direct application of the product to the wound. More preferably the product is administered to the wound by first including the product in a matrix which is itself administered to the wound. Most preferably, the product is administered to the wound by application of a pharmaceutical formulation comprising the expression product of the invention and a pharmaceutically acceptable carrier, diluent or excipient.

In another preferred embodiment, the invention relates to a method of deccelerating the rate of wound healing. The inventor recognises that there are particular surgical procedures which require a delay in wound healing so as to achieve a desirable outcome. A lysyl oxidase-mediated delay in wound healing is based on the ability to inhibit the oxidation of primary amines and therefore the ability to inhibit the cross-linking of particular molecules, where that cross-linking is essential to wound healing. Lysyl oxidase inhibitors are known, for example BAPN, although these reagents are typically noxious and therefor unsuitable for use in methods of treatment. The inventor envisages that a delay in wound healing which is mediated by the inhibition of oxidation of primary amines can be achieved by developing novel reagents which have specific anti-lysyl oxidase acitvities and which have no side-effects. Particularly suitable inhibitors of lysyl oxidase activities are anti-lysyl oxidase antibodies. These immunological reagents may be generated by raising antibodies to the expression products of the invention. The methods for the production of monoclonal antibodies or polyclonal antibodies are within the knowledge of the skilled addressee and are described in detail in standard immunological texts. Furthermore, the skilled addressee can readily determine those antibodies with anti-lysyl oxidase activities, in particular the ability to inhibit the oxidation of primary amines by performing screening of those antibodies according to the benzylamine substrate assay, tropoelastin substrate assay or tritiated tropoelastin substrate assay, as described in the accompanying Examples.

Thus, the invention provides a method of deccelerating the rate of wound healing, the method comprising the step of administering antibodies which are raised against the expression product of the invention, to a wound under conditions which allow the antibodies to substantially inhibit the oxidation of primary amines.

In another aspect embodiment, the invention relates to novel reagents for modifying the rate of wound healing. In particular, the inventor recognises that the expression products of the invention can be used to link chemical species to heterologous surfaces to substantially promote or substantially inhibit the rate of wound healing. The chemical species of interest generally include those species which contain a primary amine and which can be linked by oxidation of the primary amine to a heterologous surface, but more specifically comprise those chemical species selected from the group consisting of immunomodulatory substances including growth factors and cytokines, and substances which modify inflammatory responses or the coagulation cascade and also antibiotic substances. The heterologous surface may be a matrix comprising a complex of biomolecules, in particular elastin or tropoelastin, or a complex of non-peptide molecules. The expression product of the invention may be used to form a linkage between two chemical species which contain primary amine groups. Thus the invention has particular application to the attachment of an active ingredient to a carrier molecule.

Thus the invention provides novel reagents and formulations thereof for use in modifying the rate of wound healing, wherein the reagents are generated by oxidising a primary amine contained in a chemical species so as to link the chemical species to a heterologous surface.

In another preferred embodiment, the invention relates to the use of an expression product of the invention in the treatment or prevention of abnormal fibrosis. Lysyl oxidase has an important functional role in fibrosis and is also believed to be involved in the abnormal process of fibrosis, in particular in the fibrotic liver (Kagan H. M. 1994). The present inventor envisages the use of the expression products of the invention in promoting fibrosis so as to achieve a normal physiological outcome and inhibiting fibrosis where an abnormal outcome is to be avoided. Fibrosis may be promoted by increasing the levels of available lysyl oxidase or by. increasing the specific activity of the enzyme. For example fibrosis may be promoted by administering an expression product of the invention to a particular site so as to promote fibrosis at that site. Fibrosis may also be promoted by administering anti-lysyl oxidase antibodies which augment or enhance the specific activity of the enzyme, for example by interfering with aggregation of the protein. Fibrosis may be inhibited by inhibiting or reducing the ability of the lysyl oxidase to oxidise primary amine residues. The inventor envisages that fibrosis, as mediated through the role of lysyl oxidase in the oxidation of primary amines, could be inhibited by the use of antibodies which inhibit the oxidation reaction. As described above, the methods for the production of monoclonal antibodies or polyclonal antibodies are within the knowledge of the skilled addressee. Furthermore, the skilled addressee can readily determine those antibodies with anti-lysyl oxidase activities which either inhibit or enhance lysyl oxidase activity, in particular the ability to inhibit or enhance the oxidation of primary amines by performing screening assays according to the benzylamine substrate assay, tropoelastin substrate assay or tritiated tropoelastin substrate assay, as described in the accompanying Examples.

As described above, three separate assays are disclosed in the accompanying Examples for measuring levels of lysyl oxidase activity. The inventor recognises that the expression products of the invention could be used in a particular method so as to screen agents for the ability to inhibit or enhance lysyl oxidase acitivity. Agents which are identified as having inhibitory or enhancing effects on the specific activity of lysyl oxidase would be desirable for use in specific treatments, including wound healing or fibrosis, as described above.

Thus in a preferred embodiment, the invention provides a method for screening agents which substantially enhance or substantially inhibit the specific activity of lysyl oxidase or lysyl oxidase-like proteins, the method comprising the step of contacting the agent with an expression product of the invention and measuring the specific activity of the expression product.

To the extent that lysyl oxidase and lysyl oxidase-like proteins are involved in the oxidation of primary amines, the inventor recognises that the expression products of the invention are useful in assays for detecting substrates which contain primary amines. The expression products of the invention are also useful to quantify amounts of protein or non-protein substrates wherein those substrates contain a known number of primary amine moieties. The expression products of the invention are particularly suited to such an assay as the expression product is derived from a pure source and will therefore specifically detect primary amine groups. Furthermore, as the expression products of the invention may be variants of lysyl oxidase or a lysyl oxidase-like protein, the inventor recognises that molecules associated with a particular primary amine (for example a primary amine group displayed in a specific manner) may be specifically detected over other molecules in the sample which contain a primary amine group. The assay could be performed according to any of the three substrate assays detailed in the accompanying Examples.

Thus in a preferred embodiment, the invention relates to a method for detecting a protein or non-protein substrate in a sample, the method comprising contacting the sample with an expression product of the invention and detecting oxidation of any primary amine moieties in the sample.

In another preferred embodiment, the invention relates to a method for quantifying the amount of a protein or non-protein substrate in a sample, wherein the number of primary amine moieties per substrate molecule is known, the method comprising contacting the sample with an expression product of the invention and detecting the amount of oxidation of any primary amine moieties in the sample.

In one aspect, the lysyl oxidase, lysyl oxidase-like proteins and variants thereof may be used to cross-link a primary amine containing molecule such as tropoelastin or collagen to the surface, wherein the solid surface has primary amine groups which are available for cross-linking. In this aspect, the invention provides the use of lysyl oxidase, lysyl oxidase-like proteins and variants thereof as an agents for forming coatings on solid surfaces. The present inventor envisages that those surfaces which have primary amine groups available for cross-linking will be useful for the manufacture of synthetic tissues for example, blood vessels.

In one embodiment, it is envisaged that surface or devices could be dipped into solutions of tropoelastin and/or collagen in the presence of a lysyl oxidase, lysyl oxidase-like protein or variant of the invention.

In another embodiment, a cross-linked material could be preformed and then cross-linked to available primary amine groups on a surface, using a lysyl oxidase, lysyl oxidase-like protein or variant of the invention.

The cross-linked molecule may comprise collagen and/or tropoelastin and/or other cross-linkable primary amine containing molecules.

In another aspect, the invention provides a tissue glue, which is of use in assisting wound healing. This glue can be used as a replacement for sutures. The glue comprises an expression product of the invention and may additionally comprise at least one cross-linkable primary amine material, for example, tropoelastin and/or collagen. The glue may also be used to repair incisions in for instance, surgical applications and other body tissue defects. The glue may be applied by mixing the primary amine containing material and expression product and applying to the site.

Other uses for the expression products of the invention include the preparation of sheets or films where the product can be used as a reinforcement as well as for its biological properties. Applications could include repair of anastomoses, repair of defects in the heart. The expression products can also be used to prepare solid structures such as beads which may find application in tissue bulking applications such as in the urethra, oesaphagus or in dermatological applications where primary amine containing substances are desirably deposited in cross-linked form.

The expression products of the invention are also useful as agents for:

rrg The routes envisaged for the administration of this form of cancer therapy include gene and protein therapies in which the gene or protein is administered in accordance with protocols already developed with respect to other molecules proposed for use in gene or protein therapy. In one application category it is proposed that extracellular application of lysyl oxidase either alone or as part of a delivered complex, could reduce the growth and behaviour of cancer and other cells, including but not limited to ras-transformed cells. Lysyl oxidase administration has the potential to display the anti-cancer phenotypic potential of drugs such as azatyrosine (Krzyzosiak et al., 1992; Contente et al., 1990).

Regulating cell growth. Increased lysyl oxidase may be considered to mimic some of the functions mediated by transforming-growth-factor-beta 1 (Shibanuma et al., 1993).

Glue to join primary amine materials e.g. in surgical or veterinary applications. The expression product can be formulated in suitable carriers, buffers and other conventional delivery systems. This includes natural materials, synthetic materials and composites.

Oxidising accessible lysines (and other amines) to modify behaviour of those molecular components.

Modified lysyl oxidase to perform further reactions.

BRIEF DESCRIPTION OF ACCOMPANYING DRAWINGS

FIG. 1: Entire coding sequence (SEQ ID NO:1) for an amino acid sequence (SEQ ID NO:2) of a secreted form of human lysyl oxidase. A potential signal sequence (1 to 21 aa) is underlined (Mariani et al., 1992; Hamainen et al., 1991; Svinarich et al. 1992).

FIG. 2: DNA sequence (SEQ ID NO: 3) of a synthetic polynucleotide SHLOX encoding the amino acid sequence (SEQ ID NO: 4) of a lysyl oxidase. Restriction sites at the boundaries of each block are identified;

FIG. 3: Comparison of the synthetic sequence SHLOX with the natural sequence (GenBank HUMLOX coordinates). HUMLOX is on the upper line and SHLOX on the lower line, in each case;

FIG. 4: Sequences of synthetic oligonucleotides for SHLOX construction (5' is at the left of each sequence, and 'p' denotes phosphate). (SEQ ID NOS:5–30)

FIG. 5: Measure of lysyl oxidase activity as indicated by the production of tritiated water (TCA precipitated counts).

Figure 6:
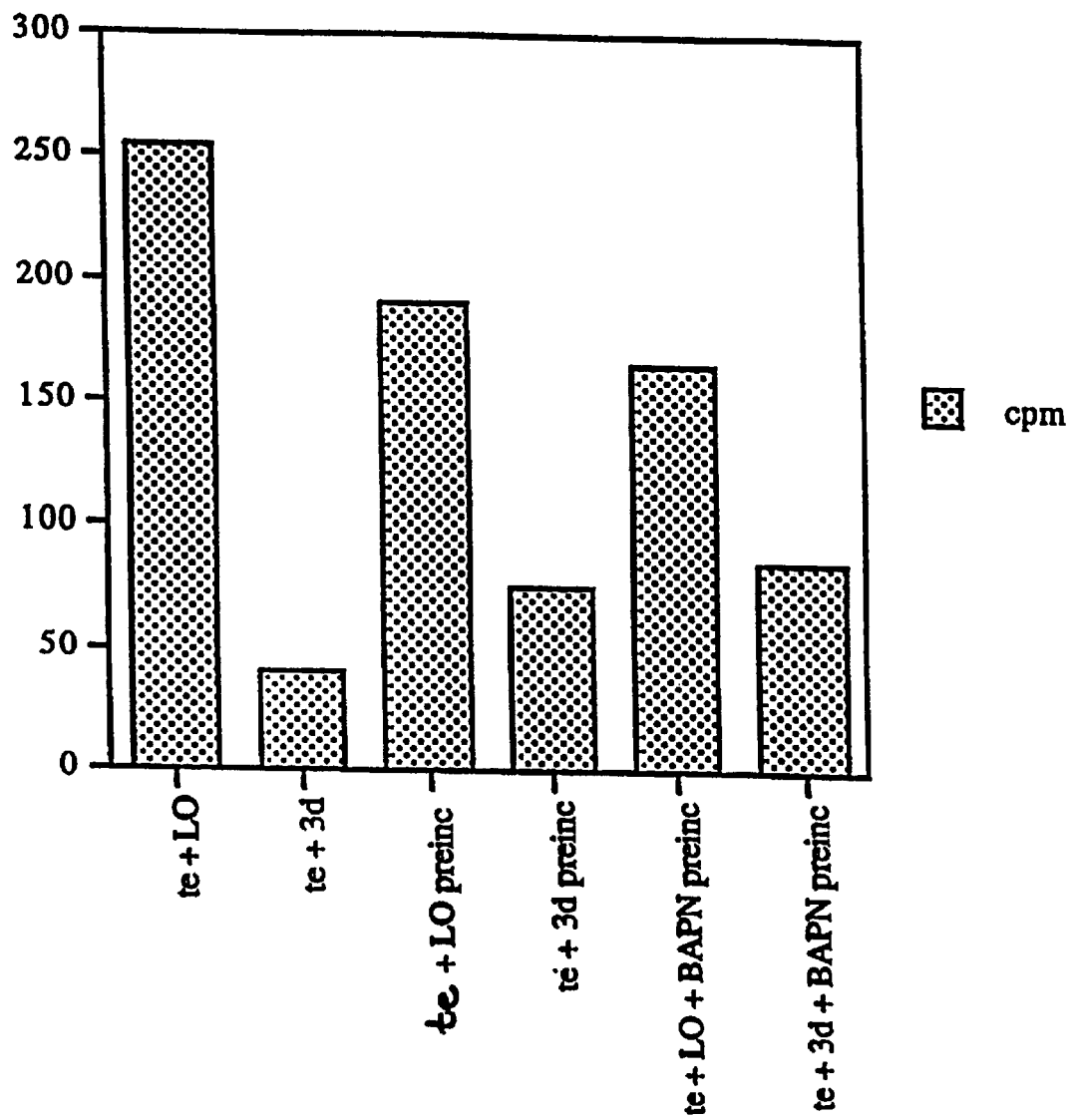

FIG. 6: Measure of lysyl oxidase activity as indicated by the production of tritiated water.

BEST METHOD OF CARRYING OUT THE INVENTION

Design of a Synthetic Lysyl Oxidase Gene

Human lysyl oxidase is typically made in human cells as a longer form, which is proteolytically processed to generate a shorter protein secreted into the extracellular space. The amino acid sequence has been compiled from data from different sources: complete sequence data which was available for cDNA encoding human lysyl oxidase (Hamalainen et al., 1991; Mariani et al., 1992), as well as partial human genome sequence (Svinarich et al., 1992). Analytical comparison of the cDNA sequences showed a discrepancy in amino acid composition which required elucidation before the synthetic gene could be made, namely Ala136(GCT) was in conflict with Arg136(CGT) of Hamalainen et al., (1991). The present inventor dealt with this by considering the genomic data, and analysing homologous regions of lysyl oxidase from different species, including rat, mouse, bovine and chicken. The choice made was later confirmed (Hamalainen et al., 1993) supporting the correction that had been made in generating the synthetic gene. The synthetic gene was designed with strategically placed restriction sites to facilitate conversion to novel derivatives and counterparts of lysyl oxidase and lysyl oxidase-related forms (Kim et al., 1995). The synthetic gene was designed with a codon usage pattern favourable to high level expression in E. coli (FIG. 2).

As lysyl oxidase is a secreted protein its cDNA derived sequence encodes a region for a signal peptide, which would not be useful for generating a functional enzyme in E. coli but rather for directing eventual transfer of the newly translated protein from inside the cell into the extracellular matrix. Furthermore the secreted pro-lysyl oxidase was thought to be cleaved by extracellular protease(s) to process the mature protein, yet it was not known if the pre-cleaved protein was active. There were doubts regarding the precise boundaries of the presumably removed signal peptide and propeptide ("leading peptide"). The likely leading peptide sequence in the N-terminal part of the lysyl oxidase sequence was determined by computer analysis and from the definitions provided by others (Trackman et al., 1990; Hamalainen et al., 1991) and was excluded from gene synthesis. Subsequent to this, further modifications were made to adjust for varied N-terminal sequences, various candidate signal sequences and eventually a better estimate of the leading peptide sequence, to generate derivatives of SHLOX, as detailed below.

Initial gene construction and cloning was conducted as described by Martin et al. (1995). The lysyl oxidase sequence of FIG. 1 was backtranslated according to a table of average codon frequencies for a group of highly expressed E. coli genes (GCG package version 7-UNIX using CodonFrequency and GenRunData: ecohighcod). The resulting codon sequence lacked rare codons. Modifications were made to the refined sequence to allow for convenient construction, cloning and analysis by adding short artificial sequences to each end of the codon-optimized gene to provide BanHI-compatible cohesive termini, an NcoI site near the 5' end of the gene, and three stop codons at the end of the open reading frame. Restriction sites were introduced into the synthetic coding sequence at 270–300 base pair intervals, dividing the gene into 4 sections of a manageable size for individual assembly, cloning and sequence analysis.

Each section was subdivided into pairs of complementary oligonucleotides. Internal junctions between oligonucleotide pairs were delineated by nucleotide overlaps, whilst the external junctions fall at the restriction enzyme cleavage points. The codon-optimized sequence and restriction sites are shown in FIG. 2, together with the encoded amino acid sequence. Oligonucleotide sequences and designations are shown in FIG. 4.

Oligonucleotide pairs 2 to 6 were made by the Sydney University Macromolecular Analysis Centre, Australia and subsequently purified by denaturing polyacrylamide gel electrophoresis (PAGE) as follows. Oligonucleotides (>85-mers) were run on PAGE containing 7M urea and 8% to 10% acrylamide (acrylamide:bisacrylamide 19:1). Samples were heated to 75° C. for 3 minutes before loading. Tracking dye (0.05% bromphenol blue, 0.05% xylene cyanole FF in deionized formamide) was loaded into an adjacent lane and electrophoresis conducted at constant power of 25 W (ca. 300 V) until the bromphenol marker was within 1 cm of the base of the gel. Product bands were visualized by UV-shadowing over a fluorescent TLC plate. Gel fragments containing purified oligonucleotides were excised and transferred to microcentrifuge tubes, crushed and soaked overnight at 60° C. in 500 μl elution buffer (0.3M sodium acetate pH7.0). A second extraction was performed with 400 μl elution buffer, for 3 to 4 hours at 60° C. and the supernatant combined with that of the first extraction. The total volume of the DNA-containing solution was reduced to approximately 400 μl by extraction with n-butanol and DNA was precipitated with 1 ml 96% ethanol. Purified oligonucleotides were collected by centrifugation, redissolved in 20 μl TE buffer and quantified by spectrophotometry. The final yield of oligonucleotide was typically 5 to 30 μg. Oligonucleotides 1 and 7 to 13 were synthesised and purified by Macromolecular Resources, USA.

Complementary oligonucleotide pairs (1 µg each, approximately 30 pmol for 95-mer) were annealed in 10 µl buffer containing 50 mM Tris.HCl pH7.5, 10 mM $MgCl_2$. The mixture was overlaid with 12 µl paraffin oil, heated to 95° C. and cooled to 16° C. over 16 h in a microprocessor-controlled heating block (Perkin Elmer Cetus Thermal Cycler). Annealed samples were transferred to clean microcentrifuge tubes and a small aliquot (1 µl) withdrawn for analysis by agarose gel electrophoresis.

For each block comprising three complementary oligonucleotide pairs (blocks 1–3), four separate reactions were set up (A+B, A+C, B+C and A+B+C). Each reaction contained 50 mM Tris.HCl, 10 mM $MgCl_2$, 1 mM ATP, 3 mM DTT, 3 µl each of the appropriate annealed oligonucleotide pairs, 0.5 µl (0.5U) T4 DNA ligase and Milli-Q water to a total volume of 10 µl. All ingredients except ATP, DTT and T4 ligase (Boehringer Mannheim, Germany) were mixed and heated to 45° C. for 5 minutes to denature cohesive termini and then cooled to room temperature before addition of the remaining components. Ligation reactions were incubated overnight at 16° C. and analysed on 2% LMT agarose gels, and ligated blocks were purified on preparative 2% LMT agarose gels with TAE running buffer. Product bands were identified under long-wave UV illumination with reference to known DNA size-standards (pBSIISK+ digested with either HaeIII or AluI) (Statagene, USA) and excised in the minimum possible volume of gel. DNA was recovered from LMT agarose fragments using GELase or agarase. Block 4 was constructed similarly, except that four instead of three complementary oligonucleotide pairs participated in the ligation reaction. Purity and yield of recovered SHLOX blocks was assessed by analytical agarose electrophoresis alongside known DNA standards.

pBSIISK+ (Stratagene) DNA was digested with appropriate restriction enzymes (FIG. 2). Inserts were purified at each stage by preparative gel electrophoresis. Plasmid DNA was isolated from agarose gels (Prep-A-Gene, Bio-Rad). Approximately 100 ng (ca. 0.05 pmol) purified plasmid fragment was added to 50 ng (ca. 0.3 pmol) synthetic block in 17 µl buffer containing 50 mM Tris.HCl pH 7.5, 10 mM $MgCl_2$ and the solution heated at 45° C. for 5 minutes to denature cohesive termini. Upon cooling to room temperature, 2 µl 10 mM ATP, 30 mM DTT and 1 µl T4 DNA ligase (1U) were added and the reaction incubated overnight at 16° C. The mixture was heated for 10 minutes at 75° C. to inactivate T4 ligase, and DNA was precipitated by adding 2.5 µl 3M sodium acetate and 250 µl ethanol to the 20 µl volume of the ligation mixture. The pellet was resuspended in a final volume of 10 µl TE, pH 8.0. Of this solution, 1 to 2 µl was used to electroporate 40 µl XL1Blue competent cells (Bio-Rad electroporation Gene Pulser and Pulse Controller; 2500V/0.05 sec). Electroporated cells were diluted with 1 ml LB media immediately after the procedure, incubated 1 hour at 37° C. and 100 µl of this was spread on agar plates containing 100 µg/ml ampicillin (LB plus ampicillin), 0.1 mM IPTG and 80 µg/ml X-gal. Recombinants were selected on the basis of a white bacterial colony phenotype, although some blue colonies were used as controls. Plasmid DNA was screened by restriction digestion and confirmed by sequencing. Plasmids containing the four lysyl oxidase blocks were designated pSHLOX1-4.

All candidate clones were screened and the mutants discarded, unless they contained mutations of potential value in future SHLOX studies. Plasmids bearing correct sequences were grown in E. coli XL1Blue cells (Bullock et al 1987), purified by CsCl-ethidium bromide density gradient centrifugation and confirmed by sequencing in both directions.

In two separate reactions, adjacent pairs of gene blocks 1+2 and 3+4 were ligated in pBSIISK+. These were designed to give recombinants α and β, respectively. Each block was excised from the appropriate plasmid and purified through agarose gel electrophoresis. 50 ng each synthetic block and 100 ng appropriately restriction enzyme cleaved complementary-tailed pBSIISK+ digest were ligated in a total of 20 µl T4 ligase buffer in the presence of 1U T4 DNA ligase overnight at 16° C. Transformants were screened by the colony white phenotype, comparative electrophoretic mobility of the intact plasmids in 0.7% TBE agarose gel and by restriction digestion. After verification of the primary structure by sequencing, pSHLOXα and pSHLOXβ were used for the final assembly of the pSHLOX gene.

pSHLOXα and pSHLOXβ plasmids were cut and the appropriate fragments containing α and β subassemblies of the intact gene of lysyl oxidase were purified from an agarose gel and ligated. Transformants were selected from LB plus ampicillin plates containing IPTG and X-gal. Correct constructs were confirmed by sequencing. The intact 1188 bp synthetic gene encoding lysyl oxidase (SHLOX) was used for all further manipulations. The construct containing full length SHLOX (FIG. 2) in pBSIISK+ was designated pSHLOXB.

The construction of SHLOX is exemplary of the methods used with other genes.

Construction of Derivatives (including shorter forms) and Placing in Various E. coli Vectors for Production 1. pGEXLOX-2T The full length SHLOX gene was excised from PSHLOXB with BamHI and purified by gel electrophoresis and GELase (Epicentre Technologies, USA). Purified fragment (100 ng) was ligated with 50 ng pGEX-2T (Medos Co Pty Ltd) in 20 µl total volume of ligase buffer using 1U of T4 DNA ligase. The vector DNA had been previously linearised with BamHI and treated with calf intestinal phosphatase (CIP; Boehringer Mannheim, Germany). Transformants were selected on LB+ampicillin plates, screened by restriction digestion and confirmed by DNA sequencing. The SHLOX gene cloned into pGEX-2T was designated pGEXLOX-2T.

2. pGEXLOX$^{m1}$

SalI and XhoI mutations were introduced (Clontech Transformer mutagenesis kit) into pGEXLOX-2T at positions −13 to +23 and 421 to 442 of the SHLOX gene using two mutagenic primers (XhoI: CTG GTT CCG CGT GGA TCC CTC GAG CAG CCG CCG CGT; SalI: ATG GTT GGT GTC GAC CCG TAC A) (Beckman Oligofax Service, Sydney). The 424 bp DNA fragment between the introduced SalI and XhoI sites was excised from the 5'-terminal region of SHLOX of pGEXLOX-2T by cutting with SalI and XhoI and the remaining plasmid DNA was gel-purified. SalI and XhoI compatible ends were ligated. Apart from GST, the resulting construct pGEXLOX$^{m1}$ was designed such that following thrombin cleavage of the expressed protein it would imitate a 'mature' SHLOX sequence, encoding a 30 kDa protein with similar size and primary structure to the natural extracellular form of lysyl oxidase (Cronshaw et.al., 1995). Following sequence confirmation and further transformation, expression was in E. coli DH5α. The resulting expressed protein was designated GST-SHLOX.

3. p3aL$^{m1}$ and p12aL$^{m1}$ pGEXLOX$^{m1}$ was treated with BamHI to release the coding sequence SHLOX$^{m1}$ (the truncated form of SHLOX). This was ligated, in each case, into the BamHI site of pET3a and pET12a plasmid vectors (Novagen Inc, USA) and the resulting constructs, p3aL$^{m1}$ and p12aL$^{m1}$ were transformed into *E. coli* HMS174 (Studier et al 1990). Transformants were plated and screened. Orientation of inserts was confirmed by restriction digestion and the regions around the cloning sites by sequencing. Following further transformation, expression was in *E. coli* BL21/DE3 (Studier et al 1990) cells for p3aL$^{m1}$ and p12aL$^{m1}$. The resulting expressed proteins were designated 3aL$^{m1}$ and 12aL$^{m1}$, respectively.

4. p3DLox

Full length SHLOX was gel-purified from pSHLOXB after BamHI digestion. pET3d vector was linearised with BamHI and dephosphorylated with CIP. Ligation of 100 ng treated vector and 50 ng purified SHLOX gene with T4 DNA ligase was conducted in 20 μl volume at 16° C. for 20 h, and the ligation mixture was used to electroporate *E. coli* HMS174. The recombinant bearing a SHLOX insert in the correct orientation was treated with NcoI to release the 842 bp fragment consisting of 39 bp of pET3d and 813 bp SHLOX. Following gel purification, the resulting linear plasmid was recircularised and cloned in *E. coli* HMS174. Clones were sequenced. The verified construct (designated p3DLox) contained the 297 bp SHLOX 3'-terminal region encoding a 13,653 Da polypeptide (designated Dlox) corresponding to a carboxyterminal sequence of human lysyl oxidase.

5. p3dL$^{m2}$

Sequences of both the 3aL$^{m1}$ and the 12aL$^{m1}$ recombinant polypeptides were not considered to precisely reflect the primary structure of mature human lysyl oxidase. Each had N-terminal extensions (of the order of 14 residues for 3aL$^{m1}$ and 24 residues for 12aL$^{m1}$) originating as a consequence of cloning and derived from their vector sequences. These were foreign to mature human lysyl oxidase. To minimise the possible interference of these extensions on the properties and structure of the recombinant mature protein, it was considered worthwhile to place the translational start site as close as possible to aspartate$_{144}$ of SHLOX. Accordingly use was made of an internal methionine$_{144}$ residue fortuitously located just three residues upstream of aspartate$_{144}$ comprising the proposed N-terminus of the processed protein. Although there was no convenient recognition site in this region, and in particular no NcoI or NdeI endonuclease restriction site in this part of the SHLOX sequence, an appropriate modification was planned by site-directed mutagenesis. The plasmid chosen for mutagenesis was pGEXSHLOX. pGEXSHLOX is identical to pGEXLOX-2T. An NcoI primer was designed (CCC GTG TTG ACG CCA TGG TTG GTG) which generated two nucleotide changes to transform the GGT ATG GTT target sequence into GCC ATG GTT. After generating the mutation, the resulting construct had two NcoI sites; the second (downstream) site was already in the SHLOX sequence. This offered a simple clone construction scheme. After screening, the mutant clone was used to prepare purified plasmid by CsCl-ethidium bromide density gradient centrifugation. From this DNA the 396 bp fragment, flanked by NcoI sites at positions 419 to 424 and 815 to 820 of the mutated SHLOX, was excised. This fragment was then inserted into pDLox. The orientation and primary structure of the recombinant was confirmed by sequencing. The resulting construct, designated p3dL$^{m2}$, was electroporated into *E. coli* BL21/DE3. The inventor recognises that the Asp 144 form can be generated by, for example, treatment of any of the pGEXLOXm1 or p3aLm1 or p12aLm1 forms with an appropriate protease, for example procollagen C-proteinase.

6. Yeast Constructs

Various constructs were made for expression in yeast, including pCNNinv (Carlsberg Research Laboratories) and pYEX-BX (AMRAD). Pichia was chosen as an alternative expression host. For pCNNinv, a form of the synthetic gene corresponding to mature secreted lysyl oxidase was generated by PCR from p12aL$^{m1}$, using primers which included at their 5' termini EagI sites. The amplification product was purified from an agarose gel using agarase, ligated to PGEM-T and transformed into *E. coli* XL1-Blue cells. Nine colonies from 16 candidate clones generated DNA that upon cutting with EagI contained bands of approx. 750 and 3004 bp. Two colonies were selected for further investigation. Manual sequencing of one of the two recombinants showed a deletion. The other clone was correct over the sequenced region. A Qiagen (GmbH, Germany) preparation of DNA from this clone was cut with EagI in parallel with pCNNinv. Both forms of DNA were purified using agarase. The cut pCNNinv was treated with calf intestinal alkaline phosphatase and purified by phenol/chloroform extraction. The vector and insert were ligated and transformed into *E. coli* XL1-Blue cells. Twenty colonies were screened using HindIII, and two colonies appeared to have inserts in the correct orientation. Spheroplasts of *Saccharomyces cerevisiae* strain DBY747 (AMRAD) were transformed separately with the two constructs, and one of these was subsequently chosen for detailed analysis. Complete DNA sequencing confirmed the correct sequence.

For cloning into PYEX-BX, the vector was cleaved with BamHI and dephosphorylated using calf intestinal alkaline phosphatase. Separately, pGEXLOX-2T was treated with restriction enzymes NotI and BamHI and the SHLOX fragment was purified from an agarose gel. This fragment was ligated to the linearised vector, after which ends were filled using deoxynucleoside triphosphates and Sequenase v2.0 (Amersham). Blunt end ligation was then carried out. Correct constructs were identified by restriction enzyme digestion followed by complete sequencing of the fragment and adjacent vector sequences.

All restriction enzymes and agarase used in this study were obtained from Boehringer Mannheim, Germany.

Preparation of Various Soluble Proteins
Growth of *E. coli* Cultures for Recombinant Lysvl Oxidase Preparation A single colony from an agar plate was grown overnight with gyrotary shaking in 3 ml LB+ampicillin media, and the entire culture was used to inoculate 250 ml 2TY medium containing 70 μgml$^{-1}$ ampicillin in a 1L conical flask. The inoculated medium was grown at 37° C. with vigorous shaking (280–290 rpm) until OD$_{600}$ ~0.6–0.8 (about 2 h) upon which expression was induced by the addition of IPTG (usually 0.4 mM IPTG for DLox, 3aL$^{m1}$ and 3dL$^{m2}$; 0.1 mM IPTG for GST-SHLOX). Prior to induction a 0.5 ml aliquot of the cell culture was withdrawn for analysis by SDS-PAGE and to confirm the absence of inclusion bodies by phase contrast microscopy. The induced cell culture was incubated under the same conditions for a further 2.5 to 3 hours then transferred to 4° C. for 30 minutes before harvesting. At this point a 4 μl aliquot was taken for analysis by phase contrast microscopy for the presence of inclusion bodies. If inclusion bodies were present, this was considered a reliable indicator of successful expression. Otherwise expression was monitored by SDS-PAGE of total bacterial protein alongside a sample collected before induction.

The culture (250 ml, 4° C.) was divided into 50 ml aliquots in polypropylene tubes and cells were harvested by centrifugation (10 minutes, 5,000 rpm, 4° C.). The supernatant was thoroughly removed and the wet pellets were weighed. A typical yield was 0.5 to 1 g packed wet cells per 50 ml culture. Pellets were either stored at −80° C. for several months, or used immediately for inclusion body purification.

Purification of Inclusion Bodies

Thawed pellets were thoroughly resuspended on ice in ~10 vol/weight of lysis buffer (50 mM TrisHCL pH8.0, 1 mM EDTA, 100 mM NaCl (usually 5 to 7 ml per tube) and lysed at 4° C. with 1 mg/ml lysozyme (added in the form of a 10-times solution in lysis buffer) for 30 minutes with constant mixing. Mixing was achieved by continuous mechanical inversion on a vertical platform at 30 to 40 rpm. To inhibit putative subsequent protease activity PMSF was then added to 0.5 mM. Quantitative cell disruption was achieved by incubation with 1% Triton-X100 (4° C., constant mixing, 30 minutes). Cell lysates showed high viscosity because of released bacterial chromosomal DNA. To reduce this effect DNA was digested until visual loss of viscosity with 0.1 mg/ml DNase in the presence of 10 mM $MgCl_2$ with constant mixing (typically 20 to 30 minutes at 4° C.). Viscosity was further reduced by sonication using three bursts of 10 seconds each in tubes immersed in ice. The extent of lysis was checked by phase contrast microscopy and if necessary the lysis time was extended and/or further sonication applied.

After centrifugation (typically 5,000 rpm, 0° to 4° C., 20 minutes) the supernatant was carefully decanted and residual drops of supernatant were removed with a tissue, taking care not to disturb the pellet. Ice-cold lysis buffer (volume equal to that of the the discarded supernatant) was mixed with the pellet containing inclusion bodies, and the pellet was dispersed either by repeated passage through a blue Gilson Pipetman or by 5 to 6 seconds sonication with a microtip at nearly maximal setting.

A second centrifugation was similarly performed and the supernatant was discarded. The washed pellet was resuspended in an equal volume of ice-cold 2M urea in 10 mM potassium phosphate buffer, pH 8.2, and incubated for 10 minutes with constant mixing at 4° C., followed by centrifugation at 5,000 rpm, 4° C., 20 minutes to collect purified inclusion body fraction in the separated pellet. This last step usually extracted only a minor fraction of protein from inclusion bodies as judged by SDS-PAGE. The pellet was kept cool until solubilisation, and never frozen. Storage of the inclusion body fraction was (unless frozen) in the presence of 6M urea at 4° C.

Solubilisation of Inclusion Body Protein

Solubilisation was achieved immediately after purification using ice-cold U6KP (6M urea in 10 mM potassium phosphate buffer, pH 8.2). The solution was autoclaved and stored at room temperature prior to use. The amount of U6KP used for solubilisation determined the eventual concentration of recombinant lysyl oxidase. Typically 5 ml U6KP was used to solubilise the pellet derived from 50 ml bacterial culture, to yield 2 to 3 mg/ml total protein. Mercaptoethanol was added to 2 to 3 mM. To help solubilisation mechanical disruption with a plastic Gilson tip was initially tried but this often led to loss of material which adhered to the inside and outside of the tip. Instead, the mixture was usually mechanically mixed by continuous mechanical inversion on a vertical platform at 30 to 40 rpm overnight, or until there was no sign of clumps. At all times the temperature was kept ~0° to 4° C.

The total protein concentration was estimated by Bradford assay, and $CuCl_2$ was added at ~5 to 10 times molar excess over estimated protein. This was usually 200 $\mu$M $CuCl_2$.

Solubilised protein stocks were used directly for protein analysis or for refolding of the protein by dialysis in various buffers, including phosphate buffers, depending on the nature of the experiment.

Refolding of Inclusion Bodies by Dialysis Against Phosphate Buffer

For dialysis against phosphate buffer 10 mm and 32 mm dialysis tubing (Selby, Australia) was usually used. Cut tubing was boiled in MilliQ water for 10 minutes and briefly soaked in dialysis buffer prior to use. 10 mM or 16 mM phosphate buffer was prepared from 1M $KH_2PO_4$ and 1M $K_2HPO_4$ solution stocks and chemical grade distilled water, with the occasionally pH adjusted with 1M KOH.

Dialysis of 2 or 3 ml of a 6M urea solution of recombinant protein (from 2 or 3 tubes, respectively) was routinely performed against 2 L urea-free buffer, with buffer changes after each dialysis. Copper-containing samples were first dialysed against buffer containing an approximately equimolar concentration of $CuCl_2$(usually 10–50 $\mu$M), in the expectation that removal of urea would be accompanied by integration of copper and bias towards a conformationally relevant form of the protein. Excess of copper was then removed in the following dialysis. After two consecutive dialyses (one against a copper-containing buffer, and the other against a copper-free buffer at pH 9.6) the dialysed material was transferred into polypropylene tubes on ice. Soluble and insoluble fractions were separated by centrifugation and analysed by SDS-PAGE. The pellet and the supernatant obtained after dialysis was stored at 4° C. without obvious protein degradation for at least 3 weeks, but some solubility changes were noticed during storage.

Protein from *S. cerevisiae* Cultures

To obtain lysyl oxidase in yeast cell pellets and lysates, a colony was grown in CSM-leu for 48 hours. To purify secreted protein, cells were separated from growth media by centrifugation, and the supernatant was dialysed against ice-cold U6KP. Cells were washed in 5 mM KPB (retained) then resuspended in 5 mM KPB plus lyticase. After incubation for 1 hour at 30° C., cells were sonicated until apparent lysis as detected by phase contrast microscopy. The pellet and lysate were separated by centrifugation. The pellet and lysates were washed with U6KP and dialysed separately against ice-cold U6KP then against KPB, pH 9.6.

PROTEIN STUDIES

To confirm the identity of the expressed protein, in each case DNA sequences were determined. Purified soluble recombinant lysyl oxidase forms were all examined by SDS-PAGE, electrospray mass spectrometry, amino acid analysis and N-terminal protein sequencing to confirm the identity of the overexpressed protein. Detailed analyses of full-length protein demonstrated the following:

(1) the protein bound copper at ~1 mole $Cu^{2+}$ per mole protein; this assay was performed by atomic absorption spectroscopy on a Varian SpectrAA-10. Protein samples were examined for protein content using a Bradford assay at 595 nm, and the ratio molar content of copper to protein was determined.

(2) the protein exists as multimers in solution; multimer formation was observed by column chromatography in experiments using either Sephadex G100 or G200, compared with protein standards. Aliquots were examined spectrophotometrically at 280 nm. Light scattering studies (Malvern Instruments S4700 version PCS v 1.26) showed size distributions, including approximately spherical particles at 30 to 56 nm.

(3) multiple peak formation by ion-exchange chromatography; multiple peaks were observed for 3dLm2 when analysed on a 100 nm×4.6 mm HperD Q column on a BioSys2000 system (Beckman, USA), using a linear NaCl gradient from ) to 0.4 M NaCl, over 9 min in the presence of 6M urea and 16 mM potassium phoshpate buffer, at 280 nm.

(4) organic cofactor formation as evidenced by redox-cycling (Paz et al., 1991), covalent radiolabel attachment of 14-C-ethylenediamine, and Raman spectroscopy of the p-nitrophenylhydrazone (5) enzyme activity including conversion of recombinant tropoelastin to aqueous-insoluble material.

In the yeast expression product studied characteristics 2 and 5 have been verified indicating that functional protein is being produced while all 5 characteristics have been verified for $E.\ coli$ expression particularly with respect to the $p3dLm^{m2}$ construct.

Levels of expression obtained have been approximately 30% of total cell protein in $E.\ coli$ and 10% of total cell protein in yeast.

Benzylamine Substrate Assay

The assay was performed according to the method of Trackman et al. 1979. The assay monitors at 250 nm the production of benzylaldehyde from benzylamine in potassium phosphate buffer at 37° C. Lysyl oxidase activity is measured spectrophotometrically at 37° C. by the conversion of benzylamine to benzaldehyde at 250 nm.

Three samples containing lysyl oxidase and benzylamine showed a slight increase in absorbance at 250 nm. In this assay the lysyl oxidase was derived from the plasmid $p3dL^{m2}$. Controls, including boiled lysyl oxidase and benzylamine, benzylamine and dialysis buffer (no enzyme) and lysyl oxidase and KPB (no substrate) showed no increase in absorbance at 250 nm.

Averaging the change in absorbance at 250 nm of the three lysyl oxidase and benzylamine samples and estimating the concentration of lysyl oxidase in each assay the specific activity of the enzyme was calculated at 0.0145 umol/min/mg. Wang et al. reports a specific activity of 0.019 U/mg.

Tropoelastin Substrate Assay

Tropoelastin resuspended in either KPB (10 mM,pH8) or PBS (10 mM PB 150 mM NaCl) was mixed at a final concentration of 10 mg/mL, with lysyl oxidase and placed at 37° C. for 2 hrs. In this assay, the lysyl oxidase was derived from the $p3dL^{m2}$ plasmid. Controls included tropoelastin+lysyl oxidase+BAPN, tropoelastin+boiled lysyl oxidase, tropoelastion+dialysis buffer, tropoelastin+buffer.

Equal amounts from each reaction were run on an 8% SDS-PAGE. On staining with Coomassie less intense tropoelastin bands were seen in the tropoelastin in KPB+LO and tropoelastin in KPB+lysyl oxidase+BAPN sample lanes compared to other lanes. This may be indicative of the presence of crosslinked tropoelastin which is too large to enter the gel. Whilst BAPN should inhibit lysyl oxidase activity, preincubation of the enzyme with BAPN for at least 2 hours at 37° C. may be required prior to assaying in order for the inhibition to be effective.

The above 2 samples and the tropoelastin+buffer control were centrifuged, the supernatant removed and the precipitate sent for amino acid analysis. The 2 samples showed a decrease in percentage of total lysine compared to the control. Tropoelastin+buffer contained 6% lysine, tropoelastin+lysyl oxidase 2.5% lysine and tropoelastin+lysyl oxidase+BAPN 2.2% lysine. This is consistent with the removal of lysine residues to form cross-links such as desmosines. Bedell- Hogan et al reports the presence of 5.6% lysine residues in recombinant tropoelastin compared to 2.4% in alkali insoluble recombinant tropoelastin.

In summary, the results show a lowering of the percentage of lysine in tropoelastin, as determined by the amino acid analysis. Furthermore, an insoluble protein was produced, consistent with the production of an elastin or elastin-like product.

Tritiated Tropoelastin Assay

Recombinant tropoelastin was prepared essentially as described Martin et al. 1995, except that BL21 cells containing pSHELF (WO 94/14958) were grown in "complete synthetic medium without lysine" (CSM-Lys), and supplemented with L-[4,5-tritium] lysine monochloride (Amersham) at 83 Ci/mmol. Accordingly, the resulting tropoelastin was radiolabelled to approximately 40,000,000 cpm/mg protein. This was lyophilised, then redissolved in assay buffer (0.1M $Na_2B_4O_7$, 0.15M NaCl, pH8) and centrifuged through Millipore Ultrafree MC for 1 hour at 7500 rpm at 4° C. The retentate was used for subsequent assays. Assays were then performed by incubation with lysyl oxidase, and assessed according to the protocol of Shackelton and Hulmes, 1990. In this assay, the lysyl oxidase was derived from the $p3dL^{m2}$ plasmid. Tritiated tropoelastin was mixed with lysyl oxidase and left at 37° C. for 16 hours. Tritiated water formed during the incubation, an indication of lysyl oxidase activity, was isolated by ultrafiltration and radioactivity quantified by liquid scintillation spectrometry. A control for endogenous lysyl oxidase-like activity in $E.\ coli$ was generated by taking an $E.\ coli$ strain containing the pET3d plasmid through the same purification procedure as that used to produce lysyl oxidase. A sample of this pET3d control was also mixed with tritiated tropoelastin. Preliminary results are consistent with some lysyl oxidase-like activity. In all cases samples containing lysyl oxidase produced more tritiated water than those containing pET3d (FIG. 5).

INDUSTRIAL APPLICABILITY

The genetic constructs of the present invention are useful in the preparation of high yields of biocompatible biospecific lysyl oxidase useful in vivo applications and other situations where catalysis of amine oxidation is required. The expression products of the invention are useful as agents for crosslinking of (but not confined to) tropoelastin and collagen both in vitro and in vivo, to join primary-amine materials e.g. in surgical or veterinary applications including natural and artificial materials, regulating cell growth, interfering with/promoting fibrosis, oxidising accessible lysines (and other amines) to modify behaviour of those molecular components and as components of assay systems designed to detect/quantify amines. Further, the genetic constructs and expression products of the invention have potential in cancer therapy.

REFERENCES

Bedell-Hogan, D., Tackman, P., Abrams, W., Rosenbloom, J. and Kagan H. (1993) J. Biol. Chem. 268, 10345–10350.

Boyd, C. D., Mariani, T. J., Kim, Y. and Csiszar, K. (1995) The size heterogeneity of human lysyl oxidase mRNA is due to alternate polyadenylation site and not alternate exon usage. *Mol. Biol. Reports*. 21, 95–103.

Bullock W. O., Fernandez J. M. and Short J. M. (1987) Biotechniques 5, 376–379

Contente, S., Kenyon, K., Rimoldi, D. and Friedman, R. M. (1990) Expression of gene rrg is associated with reversion of NIH 3T3 transformed by LTR-c-H-ras. *Science*. 249, 796–798.

Contente, S., Csiszar, K., Kenyon, K. and Friedman, R. M. (1993) Structure of the mouse lysyl oxidase gene. *Genomics*. 16, 395–400.

Cronshaw, A. D., MacBeath, J. R., Shackleton, D. R., Collins, J. F., Fothergill-Gilmore, L. A. and Hulmes, D J.

(1993) TRAMP (tyrosine rich acidic matrix protein), a protein that co-purifies with lysyl oxidase from porcine skin. Identification of TRAMP as the dermatan sulphate proteoglycan-associated 22K extracellular matrix protein. *Matrix*. 13, 255–266.

Cronshaw, A. D., Fothergill-Gilmore, L. A. and Hulmes, D. J. (1995) The proteolytic processing site of the precursor of lysyl oxidase. *Biochem. J*. 306, 279–284.

Dimaculangan, D. D., Chawla, A., Boak. A., Kagan, H. M. and Lazar, M. A. (1994) Retinoic acid prevents down-regulation of ras recision gene/lysyl oxidase early in adipocyte differentiation. *Differentiation*. 58, 47–52.

Gacheru, S. N., Trackman, P. C., Shah, M. A., O'Gara, C. Y., Spacciapoli, P., Greenaway, F. T. and Kagan, H. M. (1990) Structural and catalytic properties of copper in lysyl oxidase. *J. Biol. Chem*. 265, 19022–19027.

Gough, J. A. and Murray, N. E. (1983) Sequence diversity among related genes for recognition of specific targets in DNA molecules. *J. Mol. Biol*. 166, 1–19.

Green, R. S., Lieb, M. E., Weintraub, A. S., Gacheru, S. N., Rosenfield, C. L., Shah, S., Kagan, H. M. and Taubman, M. B. (1995) Identification of lysyl oxidase and other platelet-derived growth factor-inducible genes in vascular smooth muscle cells by differential screening. *Lab. Invest*. 73, 476–482.

Hamalainen, E. R., Jones, T. A., Sheer, D., Taskinen, K., Pihlajaniemi, T. and Kivirikko, K. I. (1991) Molecular cloning of human lysyl oxidase and assignment of the gene to chromosome 5q23.3-31.2. *Genomics*. 11, 508–516.

Hamalainen, E. R., Kemppainen, R., Pihlajaniemi, T. and Kivirikko, K. I. (1993) Structure of the human lysyl oxidase gene. *Genomics* 17, 544–548.

Kagan , H. M., (1994) Lysyl Oxidase: Mechanism, Regulation and Relationship to Liver Fibrosis. *Path. Res. Pract*. 190, 910–919.

Kagan, H. M. and Cai, P. (1995) Isolation of active site peptides of lysyl oxidase. *Meth. Enzymol*. 258, 122–132.

Kagan, H. M., Reddy, V. B., Narasimhan, N. and Csiszar, K.(1995a) Catalytic properties and structural components of lysyl oxidase. *Ciba Foundation Symposium*. 192, 100–115; discussion 115–121.

Kagan H M., Reddy, V. B., Panchenko, M. V., Nagan, N., Boak A. M., Gacheru, S. N. and Thomas, K. M. (199Sb) Expression of lysyl oxidase from cDNA constructs in mammalian cells: the propeptide region is not essential to the folding and secretion of functional enzyme. *J. Cell. Biochem*. 59, 329–338.

Kagan, H. M. and Trackman, P. C. (1991) Properties and function of lysyl oxidase. *Amer. J. Resp. Cell Mol. Biol*. 5, 206–210.

Kane, J. F., Violand, B. N., Curran, D. F., Staten, N. R., Duffin, K. L. and Bogosian, G. (1992) Novel in-frame two codon translational hop during synthesis of bovine placental lactogen in a recombinant strain of *Escherichia coli*. *Nucl. Acids. Res*. 20, 6707–6712.

Kenyon, K., Contente, S., Trackman, P. C., Tang, J., Kagan, H. M. and Friedman, R. M. (1991) Lysyl oxidase and rrg messenger RNA. *Science*. 253, 802.

Kenyon, K., Modi, W. S., Contente, S. and Friedman, R. M. (1993) A novel human cDNA with a predicted protein similar to lysyl oxidase maps to chromosome 15q24-q25. *J. Biol. Chem*. 268, 18435–18437.

Kim, Y., Boyd, C. D. and Csiszar, K. (1995) A new gene with sequence and structural similarity to the gene encoding human lysyl oxidase. *J. Biol. Chem*. 270, 7176–7182.

Krzyzosiak, W. J., Shindo-Okada, N., Teshima, H., Nakajima K. and Nishimura, S. (1992) Isolation of genes specifically expressed in flat revertant cells derived from activated ras-transformed NIH 3T3 cells by treatment with azatyrosine. *Proc. Natl. Acad. Sci*. 89, 4879–4883.

Lipman, D. J. and Pearson, W. R. (1985) Rapid and sensitive protein similarity searches. *Science* 227, 1435–1441.

Mariani, T.J., Trackman, P. C., Kagan, H. M., Eddy, R.L., Shows, T. B., Boyd, C. D. and Deak, S B. (1992) The complete derived amino acid sequence of human lysyl oxidase and assignment of the gene to chromosome 5 (extensive sequence homology with the murine ras recision gene). *Matrix*. 12, 242–248.

Martin, S. L., Vrhovski, B. and Weiss, A. S. (1995) Total synthesis and expression in *Escherichia coli* of a gene encoding human tropoelastin. *Gene* 154, 159–166.

Murray, E. E., Lotzer, J. and Eberle, M. (1989) Codon usage in plant genes. *Nucl. Acids Res*. 17, 477–498.

Nagan, N. and Kagan, H. M. (1994) Modulation of lysyl oxidase activity toward peptidyl lysine by vicinal dicarboxylic amino acid residues. Implications for collagen cross-linking. *J. Biol. Chem*. 269, 22366–22371.

Newgard, C. B., Nakano, K., Hwang, P. K. and Fletterick, R. J. (1986) Sequence analysis of the cDNA encoding human liver glycogen phosphorylase reveals tissue-specific codon usage. *Proc. Nat. Acad. Sci*. 83, 8132–8136.

Palcic, M. M,. Scaman, C. H. and Alton, G. (1995) Stereochemistry and cofactor identity status of semicarbazide-sensitive amine oxidases. *Prog. Brain Res*. 106, 41–47.

Paz, M. A., Fluckiger, R., Boak, A., Kagan, H. M. and Gallop, P. M. (1991) Specific detection of quinoproteins by redox-cycling staining. *J. Biol. Chem*. 266, 689–692.

Shackleton, D. R. and Hulmes, D. J. (1990) Purification of lysyl oxidase from piglet skin by selective interaction with Sephacryl S-200. *Biochem. J*. 266, 917–919.

Shah, M. A., Trackman, P. C., Gallop, P. M. and Kagan, H. M. (1993) Reaction of lysyl oxidase with trans-2-phenylcyclopropylamine. *J. Biol. Chem*. 268, 11580–11585.

Sharp, P. M. and Li, W. H. (1987) The codon adaptation index-a measure of directional synonymous codon usage bias, and its potential applications. *Nucl. Acids Res*. 15, 1281–1295.

Shibanuma, M., Mashimo, J., Mita A., Kuroki,T. and Nose, K. (1993) Cloning from a mouse osteoblastic cell line of a set of transforming-growth-factor-beta 1-regulated genes, one of which seems to encode a follistatin-related polypeptide. *Eur. J. Biochem*. 217, 13–19.

Studier, F. W., Rosenberg, A. H., Dunn, J. J. and Dubendorff, J. W. (1990) Use of T7 RNA polymerase to direct expression of cloned genes. *Meth. Enzymol*. 185, 60–89.

Svinarich, D. M., Twomey, T. A., Macauley, S. P., Krebs, C. J., Yang, T. P. and Krawetz, S. A. (1992) Characterization of the human lysyl oxidase gene locus. *J. Biol. Chem*. 267, 14382–14387.

Tanizawa, K. (1995) Biogenesis of novel quinone coenzymes. *J. Biochem*. 118, 671–678.

Trackman, P. C., Pratt, A. M., Wolanski, A., Tang, S. S., Offner,G. D., Troxler, R. F. and Kagan, H. M. (1990) Cloning of rat aorta lysyl oxidase CDNA: complete codons and predicted amino acid sequence. *Biochemistry* 29, 4863–4870 [published erratum appears in (1991) *Biochemistry* 30, 8282].

Williamson, P. R., Moog, R. S., Dooley, D. M. and Kagan, H. M. (1986) Evidence for pyrroloquinolinequinone as the carbonyl cofactor in lysyl oxidase by absorption and resonance Raman spectroscopy. *J. Biol. Chem*. 261, 16302–16305.

Wu, Y., Rich, C. B., Lincecum, J., Trackman, P. C., Kagan, H. M. and Foster, J. A. (1992) Characterization and developmental expression of chick aortic lysyl oxidase. *J. Biol. Chem.* 267, 24199–24206.

Zhang, S. P., Zubay, G. and Goldman, E. (1991) Low-usage codons in *Escherichia coli*, yeast, fruit fly and primates. *Gene*. 105, 61–72.

Kim, Y., Boyd, C. D., and Csiszar, K. (1995) A new gene with sequence and structural similarity to the gene encoding human lysyl oxidase. *J. Biol. Chem.* 270, 7176–7182.

Wang, S. X., Mure, M., Medzihradsky, K. F., Burlingame, A. L., Brown, D. E. Dooley, D. M., SMith, A. J., Kagan, H. M. and Klinman, J. P (1996) A cross linked cofactor in lysy loxidase:redox function for amino acid side chains. *Science*. 273, 1078–1084.

Trackman, P. C. and Kagan, H. M. (1979) Nonpeptidyl amine inhibitors are substrates of lysyl oxidase. *J. Biol. Chem.* 254, 7831–7836.

What is claimed is:

1. A synthetic polynucleotide which encodes human lysyl oxidase, the polynucleotide having CAI score of at least 0.30 in *E. coli*, wherein the polynucleotide consists of the nucleotide sequence shown in SEQ ID NO:3.

2. A synthetic polynucleotide which comprises the nucleotide sequence shown in SEQ ID NO:3.

3. A fragment of a synthetic polynuclcotide according to claim 1 which encodes an amino acid sequence capable of catalyzing the oxidation of primary amines.

4. A fragment according to claim 3, wherein the 5' terminal codon of the fragment encodes amino acid residue number 141 of lysyl oxidase.

5. A fragment according to claim 3, wherein the 5' terminal codon of the fragment encodes amino acid residue number 144 of lysyl oxidase.

6. A host cell comprising a synthetic polynucleotide according to claim 1 or 2.

7. A host cell comprising a fragment according to any of claims 3 to 5.

* * * * *

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 1251 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "nucleic acid"

(iii) HYPOTHETICAL: YES (iv) ANTI-SENSE: YES (xi) SEQUENCE DESCRIPTION: SEQ ID NO:1:

```
ATGCGCTTCG CCTGGACCGT GCTCCTGCTC GGGCCTTTGC AGCTCTGCGC GCTAGTGCAC      60

TGCGCCCCTC CCGCCGCCGG CCAACAGCAG CCCCCGCGCG AGCCGCCGGC GGCTCCGGGC     120

GCCTGGCGCC AGCAGATCCA ATGGGAGAAC AACGGGCAGG TGTTCAGCTT GCTGAGCCTG     180

GGCTCACAGT ACCAGCCTCA GCGCCGCCGG GACCCGGGCG CCGCCGTCCC TGGTGCAGCC     240

AACGCCTCCG CCCAGCAGCC CCGCACTCCG ATCCTGCTGA TCCGCGACAA CCGCACCGCC     300

GCGGCGCGAA CGCGGACGGC CGGCTCATCT GGAGTCACCG CTGGCCGCCC CAGGCCCACC     360

GCCCGTCACT GGTTCCAAGC TGGCTACTCG ACATCTAGAG CCCGCGAACG TGGCGCCTCG     420

CGCGCGGAGA ACCAGACAGC GCCGGGAGAA GTTCCTGCGC TCAGTAACCT GCGGCCGCCC     480

AGCCGCGTGG ACGGCATGGT GGGCGACGAC CCTTACAACC CCTACAAGTA CTCTGACGAC     540

AACCCTTATT ACAACTACTA CGATACTTAT GAAAGGCCCA GACCTGGGGG CAGGTACCGG     600

CCCGGATACG GCACTGGCTA CTTCCAGTAC GGTCTCCCAG ACCTGGTGGC CGACCCCTAC     660

TACATCCAGG CGTCCACGTA CGTGCAGAAG ATGTCCATGT ACAACCTGAG ATGCGCGGCG     720

GAGGAAAACT GTCTGGCCAG TACAGCATAC AGGGCAGATG TCAGAGATTA TGATCACAGG     780

GTGCTGCTCA GATTTCCCCA AAGAGTGAAA AACCAAGGGA CATCAGATTT CTTACCCAGC     840

CGACCAAGAT ATTCCTGGGA ATGGCACAGT TGTCATCAAC ATTACCACAG TATGGATGAG     900

TTTAGCCACT ATGACCTGCT TGATGCCAAC ACCCAGAGGA GAGTGGCTGA AGGCCACAAA     960

GCAAGTTTCT GTCTTGAAGA CACATCCTGT GACTATGGCT ACCACAGGCG ATTTGCATGT    1020

ACTGCACACA CACAGGGATT GAGTCCTGGC TGTTATGATA CCTATGGTGC AGACATAGAC    1080

TGCCAGTGGA TTGATATTAC AGATGTAAAA CCTGGAAACT ATATCCTAAA GGTCAGTGTA    1140

AACCCCAGCT ACCTGGTTCC TGAATCTGAC TATACCAACA ATGTTGTGCG CTGTGACATT    1200

CGCTACACAG GACATCATGC GTATGCCTCA GGCTGCACAA TTTCACCGTA T             1251
```

(2) INFORMATION FOR SEQ ID NO:2:

(i) SEQUENCE CHARACTERISTICS:
        (A) LENGTH: 417 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (xi) SEQUENCE DESCRIPTION: SEQ ID NO:2:

```
Met Arg Phe Ala Trp Thr Val Leu Leu Leu Gly Pro Leu Gln Leu Cys
  1               5                  10                  15

Ala Leu Val His Cys Ala Pro Pro Ala Ala Gly Gln Gln Gln Pro Pro
             20                  25                  30

Arg Glu Pro Pro Ala Ala Pro Gly Ala Trp Arg Gln Gln Ile Gln Trp
         35                  40                  45

Glu Asn Asn Gly Gln Val Phe Ser Leu Leu Ser Leu Gly Ser Gln Tyr
 50                  55                  60

Gln Pro Gln Arg Arg Arg Asp Pro Gly Ala Ala Val Pro Gly Ala Ala
 65                  70                  75                  80

Asn Ala Ser Ala Gln Gln Pro Arg Thr Pro Ile Leu Leu Ile Arg Asp
                 85                  90                  95

Asn Arg Thr Ala Ala Ala Arg Thr Arg Thr Ala Gly Ser Ser Gly Val
                100                 105                 110

Thr Ala Gly Arg Pro Arg Pro Thr Ala Arg His Trp Phe Gln Ala Gly
            115                 120                 125

Tyr Ser Thr Ser Arg Ala Arg Glu Arg Gly Ala Ser Arg Ala Glu Asn
130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Pro Tyr Asn Pro Tyr Lys
                165                 170                 175

Tyr Ser Asp Asp Asn Pro Tyr Tyr Asn Tyr Tyr Asp Thr Tyr Glu Arg
                180                 185                 190

Pro Arg Pro Gly Gly Arg Tyr Arg Pro Gly Tyr Gly Thr Gly Tyr Phe
            195                 200                 205

Gln Tyr Gly Leu Pro Asp Leu Val Ala Asp Pro Tyr Tyr Ile Gln Ala
        210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
            260                 265                 270

Gly Thr Ser Asp Phe Leu Pro Ser Arg Pro Arg Tyr Ser Trp Glu Trp
        275                 280                 285

His Ser Cys His Gln His Tyr His Ser Met Asp Glu Phe Ser His Tyr
    290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335
```

```
Arg Phe Ala Cys Thr Ala His Thr Gln Gly Leu Ser Pro Gly Cys Tyr
            340                 345                 350

Asp Thr Tyr Gly Ala Asp Ile Asp Cys Gln Trp Ile Asp Ile Thr Asp
        355                 360                 365

Val Lys Pro Gly Asn Tyr Ile Leu Lys Val Ser Val Asn Pro Ser Tyr
    370                 375                 380

Leu Val Pro Glu Ser Asp Tyr Thr Asn Asn Val Val Arg Cys Asp Ile
385                 390                 395                 400

Arg Tyr Thr Gly His His Ala Tyr Ala Ser Gly Cys Thr Ile Ser Pro
            405                 410                 415

Tyr (2) INFORMATION FOR SEQ ID NO:3:

(i) SEQUENCE CHARACTERISTICS:
        (A) LENGTH: 1184 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "nucleic acid"

(iii) HYPOTHETICAL: YES (iv) ANTI-SENSE: YES (xi) SEQUENCE DESCRIPTION: SEQ ID NO:3:
```

| | |
|---|---|
| GATCCCAGCA GCAGCCGCCG CGTGAACCGC CGGCTGCTCC GGGTGCTTGG CGTCAGCAGA | 60 |
| TCCAGTGGGA AAACAACGGT CAGGTTTTCT CCCTGCTGTC CCTGGGTTCC CAGTACCAGC | 120 |
| CGCAGCGTCG TCGTGACCCG GGTGCTGCTG TTCCGGGTGC TGCTAACGCT TCCGCTCAGC | 180 |
| AGCCGCGTAC CCCGATCCTG CTGATCCGTG ACAACCGTAC CGCGGCCGCT CGTACCCGTA | 240 |
| CCGCTGGTTC CTCCGGTGTT ACTGCAGGTC GTCCGCGTCC GACCGCGCGC CACTGGTTCC | 300 |
| AGGCTGGTTA CTCCACCTCC CGTGCTCGTG AAGCTGGTGC TTCCCGTGCT GAAAACCAGA | 360 |
| CCGCTCCGGG TGAAGTTCCA GCGCTGTCCA ACCTGCGTCC GCCGTCCCGT GTTGACGGTA | 420 |
| TGGTTGGTGA CGACCCGTAC AACCCGTACA AGTACTCCGA CGACAACCCG TACTACAACT | 480 |
| ACTACGACAC CTACGAGCGC CCGCGTCCGG GTGGTCGTTA CCGTCCGGGT TACGGTACCG | 540 |
| GTTACTTCCA GTACGGTCTG CCGGACCTGG TTGCTGACCC GTACTACATC CAGGCTTCCA | 600 |
| CCTACGTTCA GAAAATGTCC ATGTACAACC TGCGTTGCGC TGCTGAAGAA AACTGCCTGG | 660 |
| CTTCCACCGC TTACCGTGCT GACGTTCGTG ACTACGACCA CCGTGTTCTG CTGCGTTTCC | 720 |
| CGCAGCGTGT TAAAAACCAG GGCACCTCCG ACTTCCTGCC GTCCCGTCCG CGTTACTCCT | 780 |
| GGGAATGGCA CTCCTGCCAC CAGCACTACC ACTCCATGGA CGAATTCTCC CACTACGACC | 840 |
| TGCTGGACGC TAACACCCAG CGTCGTGTTG CTGAAGGTCA CAAAGCTTCC TTCTGCCTGG | 900 |
| AAGACACCTC CTGCGACTAC GGTTACCACC GTCGTTTCGC TTGCACCGCT CACACCCAGG | 960 |
| GTCTGTCCCC GGGTTGCTAC GACACCTACG GTGCTGACAT CGACTGCCAG TGGATCGACA | 1020 |
| TCACCGACGT TAAACCGGGT AACTACATCC TGAAAGTTTC CGTTAACCCG TCCTACCTGG | 1080 |
| TTCCGGAATC CGACTACACC AACAACGTGG TTCGTTGCGA TATCCGTTAC ACCGGTCACC | 1140 |
| ACGCTTACGC TTCCGGTTGC ACCATCTCCC CGTACTAATG ATAG | 1184 |

(2) INFORMATION FOR SEQ ID NO:4:

(i) SEQUENCE CHARACTERISTICS:
        (A) LENGTH: 391 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (xi) SEQUENCE DESCRIPTION: SEQ ID NO:4:

```
Ser Gln Gln Gln Pro Pro Arg Glu Pro Pro Ala Ala Pro Gly Ala Trp
 1               5                  10                  15

Arg Gln Gln Ile Gln Trp Glu Asn Asn Gly Gln Val Phe Ser Leu Leu
            20                  25                  30

Ser Leu Gly Ser Gln Tyr Gln Pro Gln Arg Arg Asp Pro Gly Ala
            35                  40                  45

Ala Val Pro Gly Ala Ala Asn Ala Ser Ala Gln Gln Pro Arg Thr Pro
        50                  55                  60

Ile Leu Leu Ile Arg Asp Asn Arg Thr Ala Ala Arg Thr Arg Thr
 65                  70                  75                  80

Ala Gly Ser Ser Gly Val Thr Ala Gly Arg Pro Arg Thr Ala Arg
                85                  90                  95

His Trp Phe Gln Ala Gly Tyr Ser Thr Ser Arg Ala Arg Glu Ala Gly
            100                 105                 110

Ala Ser Arg Ala Glu Asn Gln Thr Ala Pro Gly Glu Val Pro Ala Leu
        115                 120                 125

Ser Asn Leu Arg Pro Pro Ser Arg Val Asp Gly Met Val Gly Asp Asp
130                 135                 140

Pro Tyr Asn Pro Tyr Lys Tyr Ser Asp Asp Asn Pro Tyr Tyr Asn Tyr
145                 150                 155                 160

Tyr Asp Thr Tyr Glu Arg Pro Arg Pro Gly Gly Arg Tyr Arg Pro Gly
                165                 170                 175

Tyr Gly Thr Gly Tyr Phe Gln Tyr Gly Leu Pro Asp Leu Val Ala Asp
            180                 185                 190

Pro Tyr Tyr Ile Gln Ala Ser Thr Tyr Val Gln Lys Met Ser Met Tyr
        195                 200                 205

Asn Leu Arg Cys Ala Ala Glu Glu Asn Cys Leu Ala Ser Thr Ala Tyr
210                 215                 220

Arg Ala Asp Val Arg Asp Tyr Asp His Arg Val Leu Leu Arg Phe Pro
225                 230                 235                 240

Gln Arg Val Lys Asn Gln Gly Thr Ser Asp Phe Leu Pro Ser Arg Pro
                245                 250                 255

Arg Tyr Ser Trp Glu Trp His Ser Cys His Gln His Tyr His Ser Met
            260                 265                 270

Asp Glu Phe Ser His Tyr Asp Leu Leu Asp Ala Asn Thr Gln Arg Arg
        275                 280                 285

Val Ala Glu Gly His Lys Ala Ser Phe Cys Leu Glu Asp Thr Ser Cys
290                 295                 300

Asp Tyr Gly Tyr His Arg Arg Phe Ala Cys Thr Ala His Thr Gln Gly
305                 310                 315                 320
```

```
Leu Ser Pro Gly Cys Tyr Asp Thr Tyr Gly Ala Asp Ile Asp Cys Gln
            325                 330                 335

Trp Ile Asp Ile Thr Asp Val Lys Pro Gly Asn Tyr Ile Leu Lys Val
            340                 345                 350

Ser Val Asn Pro Ser Tyr Leu Val Pro Glu Ser Asp Tyr Thr Asn Asn
        355                 360                 365

Val Val Arg Cys Asp Ile Arg Tyr Thr Gly His His Ala Tyr Ala Ser
    370                 375                 380

Gly Cys Thr Ile Ser Pro Tyr
385             390
```

(2) INFORMATION FOR SEQ ID NO:5:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:5:

```
GATCCCAGCA GCAGCCGCCG CGTGAACCGC CGGCTGCTCC GGGTGCTTGG CGTCAGCAGA      60

TCCAGTGGGA AACAACGGT CAGGTTTTCT CCCTG                                 95
```

(2) INFORMATION FOR SEQ ID NO:6:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:6:

```
CTGTCCCTGG GTTCCCAGTA CCAGCCGCAG CGTCGTCGTG ACCCGGGTGC TGCTGTTCCG      60

GGTGCTGCTA ACGCTTCCGC TCAGC                                           85
```

(2) INFORMATION FOR SEQ ID NO:7:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:7:

```
AGCCGCGTAC CCCGATCCTG CTGATCCGTG ACAACCGTAC CGCGGCCGCT CGTACCCGTA      60

CCGCTGGTTC CTCCGGTGTT ACTGCA                                          86

(2) INFORMATION FOR SEQ ID NO:8:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:8:

GGTCGTCCGC GTCCGACCGC GCGCCACTGG TTCCAGGCTG GTTACTCCAC CTCCCGTGCT      60

CGTGAAGCTG GTGCTTCCCG TGCTGAAAAC CAG                                  93

(2) INFORMATION FOR SEQ ID NO:9:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:9:

ACCGCTCCGG GTGAAGTTCC AGCGCTGTCC AACCTGCGTC CGCCGTCCCG TGTTGACGGT      60

ATGGTTGGTG ACGACCCGTA CAACCCGTAC A                                    91

(2) INFORMATION FOR SEQ ID NO:10:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:10:

AGTACTCCGA CGACAACCCG TACTACAACT ACTACGACAC CTACGAGCGC CCGCGTCCGG      60

GTGGTCGTTA CCGTCCGGGT TACGGTAC                                        88

(2) INFORMATION FOR SEQ ID NO:11:

(i) SEQUENCE CHARACTERISTICS:
        (A) LENGTH: 88 base pairs
        (B) TYPE: nucleic acid
        (C) STRANDEDNESS: single
        (D) TOPOLOGY: linear
```

(ii) MOLECULE TYPE: other nucleic acid
            (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:11:

CGGTTACTTC CAGTACGGTC TGCCGGACCT GGTTGCTGAC CCGTACTACA TCCAGGCTTC      60

CACCTACGTT CAGAAAATGT CCATGTAC                                        88

(2) INFORMATION FOR SEQ ID NO:12:

(i) SEQUENCE CHARACTERISTICS:
            (A) LENGTH: 97 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:12:

AACCTGCGTT GCGCTGCTGA AGAAAACTGC CTGGCTTCCA CCGCTTACCG TGCTGACGTT      60

CGTGACTACG ACCACCGTGT TCTGCTGCGT TTCCCGC                              97

(2) INFORMATION FOR SEQ ID NO:13:

(i) SEQUENCE CHARACTERISTICS:
            (A) LENGTH: 99 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:13:

AGCGTGTTAA AAACCAGGGC ACCTCCGACT TCCTGCCGTC CGTCCGCGT TACTCCTGGG       60

AATGGCACTC CTGCCACCAG CACTACCACT CCATGGACG                            99

(2) INFORMATION FOR SEQ ID NO:14:

(i) SEQUENCE CHARACTERISTICS:
            (A) LENGTH: 99 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:14:

AATTCTCCCA CTACGACCTG CTGGACGCTA ACACCCAGCG TCGTGTTGCT GAAGGTCACA      60

AAGCTTCCTT CTGCCTGGAA GACACCTCCT GCGACTACG                            99

(2) INFORMATION FOR SEQ ID NO:15:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:15:

```
GTTACCACCG TCGTTTCGCT TGCACCGCTC ACACCCAGGG TCTGTCCCCG GGTTGCTACG      60

ACACCTACGG TGCTGACATC GACTGCCAGT GGA                                  93
```

(2) INFORMATION FOR SEQ ID NO:16:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:16:

```
TCGACATCAC CGACGTTAAA CCGGGTAACT ACATCCTGAA AGTTTCCGTT AACCCGTCCT      60

ACCTGGTTCC GGAATCCGAC TACACCAACA ACG                                  93
```

(2) INFORMATION FOR SEQ ID NO:17:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:17:

```
TGGTTCGTTG CGATATCCGT TACACCGGTC ACCACGCTTA CGCTTCCGGT TGCACCATCT      60

CCCCGTACTA ATGATAG                                                    77
```

(2) INFORMATION FOR SEQ ID NO:18:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:18:

GAAAACCTGA CCGTTGTTTT CCCACTGGAT CTGCTGACGC CAAGCACCCG GAGCAGCCGG    60

CGGTTCACGC GGCGGCTGCT GCTGG    85

(2) INFORMATION FOR SEQ ID NO:19:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:19:

CGGAAGCGTT AGCAGCACCC GGAACAGCAG CACCCGGGTC ACGACGACGC TGCGGCTGGT    60

ACTGGGAACC CAGGGACAGC AGGGA    85

(2) INFORMATION FOR SEQ ID NO:20:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:20:

GTAACACCGG AGGAACCAGC GGTACGGGTA CGAGCGGCCG CGGTACGGTT GTCACGGATC    60

AGCAGGATCG GGTACGCGG CTGCTGAG    88

(2) INFORMATION FOR SEQ ID NO:21:

(i) SEQUENCE CHARACTERISTICS:
            (A) LENGTH: 91 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:21:

TTCAGCACGG GAAGCACCAG CTTCACGAGC ACGGGAGGTG GAGTAACCAG CCTGGAACCA    60

GTGGCGCGCG GTCGGACGCG GACGACCTGC A    91

(2) INFORMATION FOR SEQ ID NO:22:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:22:

```
GTTGTACGGG TCGTCACCAA CCATACCGTC AACACGGGAC GGCGGACGCA GGTTGGACAG      60

CGCTGGAACT TCACCCGGAG CGGTCTGGTT                                      90
```

(2) INFORMATION FOR SEQ ID NO:23:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:23:

```
CGTAACCCGG ACGGTAACGA CCACCCGGAC GCGGGCGCTC GTAGGTGTCG TAGTAGTTGT      60

AGTACGGGTT GTCGTCGGAG TACTTGTACG G                                    91
```

(2) INFORMATION FOR SEQ ID NO:24:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:24:

```
GCAGGTTGTA CATGGACATT TTCTGAACGT AGGTGGAAGC CTGGATGTAG TACGGGTCAG      60

CAACCAGGTC CGGCAGACCG TACTGGAAGT ACCGGTAC                             98
```

(2) INFORMATION FOR SEQ ID NO:25:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

-continued

```
    (iii) HYPOTHETICAL: YES (iv) ANTI-SENSE: YES (xi) SEQUENCE DESCRIPTION: SEQ ID NO:25:

ACACGCTGCG GGAAACGCAG CAGAACACGG TGGTCGTAGT CACGAACGTC AGCACGGTAA      60

GCGGTGGAAG CCAGGCAGTT TTCTTCAGCA GCGCAAC                              97

(2) INFORMATION FOR SEQ ID NO:26:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:26:

AATTCGTCCA TGGAGTGGTA GTGCTGGTGG CAGGAGTGCC ATTCCCAGGA GTAACGCGGA      60

CGGGACGGCA GGAAGTCGGA GGTGCCCTGG TTTTTA                               96

(2) INFORMATION FOR SEQ ID NO:27:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:27:

GCAGGAGGTG TCTTCCAGGC AGAAGGAAGC TTTGTGACCT TCAGCAACAC GACGCTGGGT      60

GTTAGCGTCC AGCAGGTCGT AGTGGGAG                                        88

(2) INFORMATION FOR SEQ ID NO:28:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:28:

GGCAGTCGAT GTCAGCACCG TAGGTGTCGT AGCAACCCGG GGACAGACCC TGGGTGTGAG      60

CGGTGCAAGC GAAACGACGG TGGTAACCGT AGTC                                 94
```

(2) INFORMATION FOR SEQ ID NO:29:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:29:

```
TGGTGTAGTC GGATTCCGGA ACCAGGTAGG ACGGGTTAAC GGAAACTTTC AGGATGTAGT      60

TACCCGGTTT AACGTCGGTG ATGTCGATCC ACT                                  93
```

(2) INFORMATION FOR SEQ ID NO:30:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: YES (iv) ANTI-SENSE: YES (xi) SEQUENCE DESCRIPTION: SEQ ID NO:30:

```
GATCCTATCA TTAGTACGGG GAGATGGTGC AACCGGAAGC GTAAGCGTGG TGACCGGTGT      60

AACGGATATC GCAACGAACC ACGTTGT                                         87
```